United States Patent
Leff et al.

(10) Patent No.: US 10,130,395 B2
(45) Date of Patent: Nov. 20, 2018

(54) MODULAR UNIPLANAR PEDICLE SCREW ASSEMBLY FOR USE WITH A POLYAXIAL BONE FASTENER

(71) Applicant: GLOBUS MEDICAL, INC., Audubon, PA (US)

(72) Inventors: David Leff, Conshohocken, PA (US); Patrick Nolan, Palmyra, NJ (US); Liana Mari, Philadelphia, PA (US); Noah Gross, Philadelphia, PA (US); Khiem Pham, Chalfont, PA (US); Aditya Ingalhalikar, King of Prussia, PA (US); Kurt Faulhaber, Plymouth Meeting, PA (US)

(73) Assignee: Globus Medical, Inc., Audubon, PA (US)

( * ) Notice: Subject to any disclaimer, the term of this patent is extended or adjusted under 35 U.S.C. 154(b) by 11 days.

(21) Appl. No.: 14/827,905

(22) Filed: Aug. 17, 2015

(65) Prior Publication Data
US 2017/0049484 A1 Feb. 23, 2017

(51) Int. Cl.
*A61B 17/70* (2006.01)
*A61B 17/56* (2006.01)

(52) U.S. Cl.
CPC ...... *A61B 17/7038* (2013.01); *A61B 17/7037* (2013.01); *A61B 2017/564* (2013.01)

(58) Field of Classification Search
CPC .................................................. A61B 17/7038
USPC ....................................................... 606/267
See application file for complete search history.

(56) References Cited

U.S. PATENT DOCUMENTS

| | | | | |
|---|---|---|---|---|
| 5,499,983 A | * | 3/1996 | Hughes | A61B 17/701 403/298 |
| 8,430,914 B2 | * | 4/2013 | Spratt | A61B 17/7037 606/265 |
| 8,632,571 B2 | * | 1/2014 | Kraus | A61B 17/7032 606/264 |
| 2003/0105460 A1 | * | 6/2003 | Crandall | A61B 17/7035 606/256 |
| 2006/0155278 A1 | * | 7/2006 | Warnick | A61B 17/7037 606/278 |
| 2008/0262556 A1 | | 10/2008 | Jacofsky et al. | |
| 2009/0018591 A1 | | 1/2009 | Hawkes et al. | |

(Continued)

FOREIGN PATENT DOCUMENTS

FR 2958531 A1 * 10/2011 ......... A61B 17/7032

*Primary Examiner* — Jan Christopher Merene

(57) ABSTRACT

A modular uniplanar pedicle screw assembly for use with a polyaxial bone fastener. The modular assembly comprises a uniplanar tulip assembly adapted to be coupled to a head of the polyaxial bone fastener, wherein the uniplanar tulip assembly includes a longitudinal slot. The modular assembly further includes an adapter having a lower portion and an upper portion. The lower portion is sized and shaped to be received in a recess of the bone fastener head. The upper portion extends from the lower portion and is adapted to slide along the longitudinal slot of the uniplanar tulip assembly to allow movement of the uniplanar tulip assembly in a first plane along a direction that is parallel to a longitudinal axis of the longitudinal slot, the longitudinal slot preventing movement of the uniplanar tulip assembly in a second plane lateral to the first plane relative to the bone fastener.

13 Claims, 19 Drawing Sheets

(56) References Cited

U.S. PATENT DOCUMENTS

| | | | |
|---|---|---|---|
| 2010/0030224 A1* | 2/2010 | Winslow | A61B 17/7023 606/104 |
| 2011/0178558 A1 | 7/2011 | Barry | |
| 2013/0096624 A1* | 4/2013 | Di Lauro | A61B 17/7011 606/279 |
| 2013/0110180 A1 | 5/2013 | Doubler et al. | |
| 2013/0184819 A1* | 7/2013 | Donnelly | A61F 2/0811 623/13.14 |
| 2014/0012336 A1* | 1/2014 | Biedermann | A61B 17/844 606/313 |
| 2014/0188173 A1 | 7/2014 | Mishra et al. | |
| 2014/0343617 A1* | 11/2014 | Hannen | A61B 17/8605 606/306 |
| 2015/0223844 A1* | 8/2015 | Leff | A61B 17/705 606/265 |

\* cited by examiner

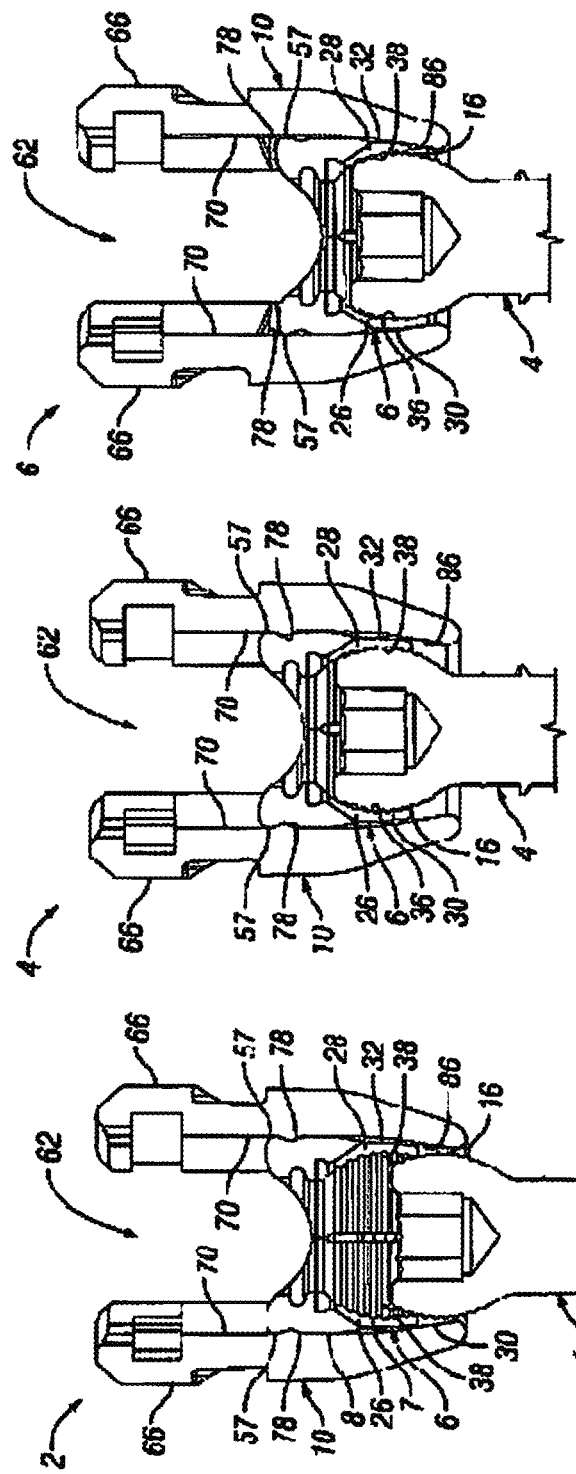

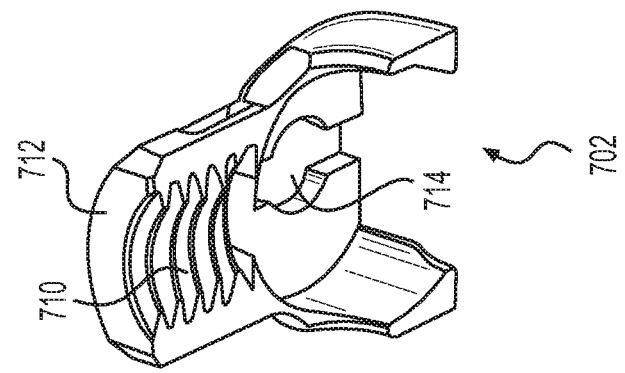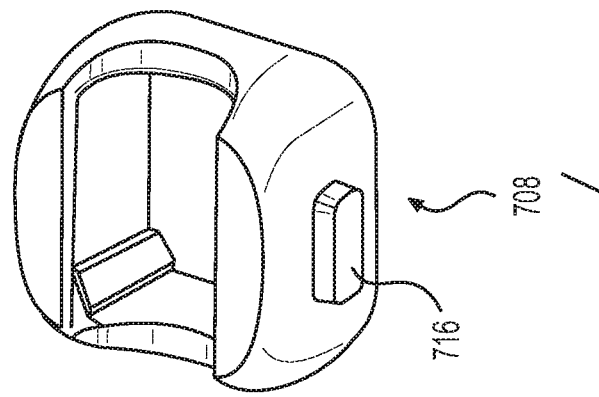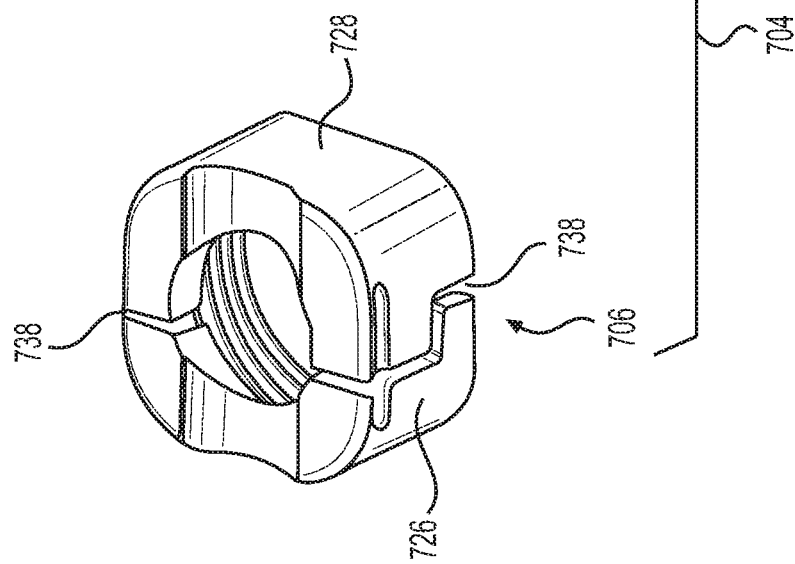
FIG. 20

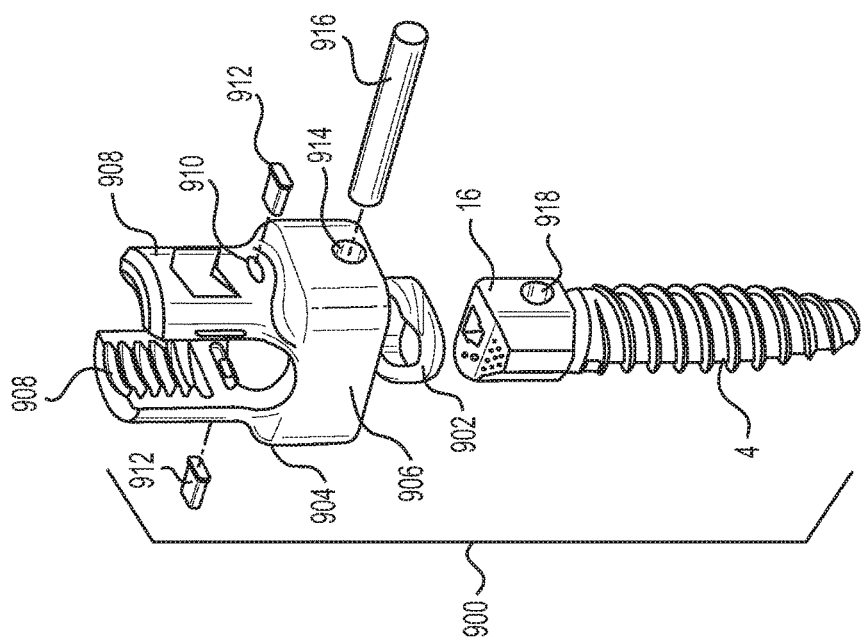
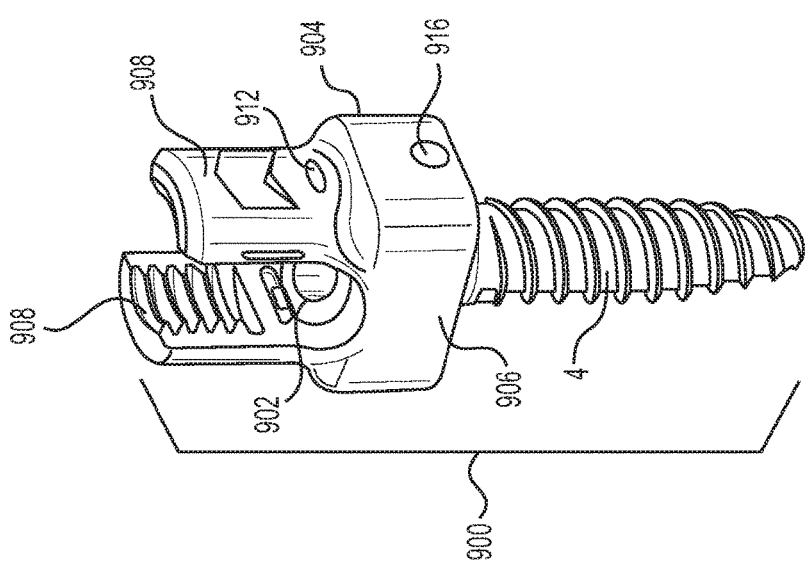

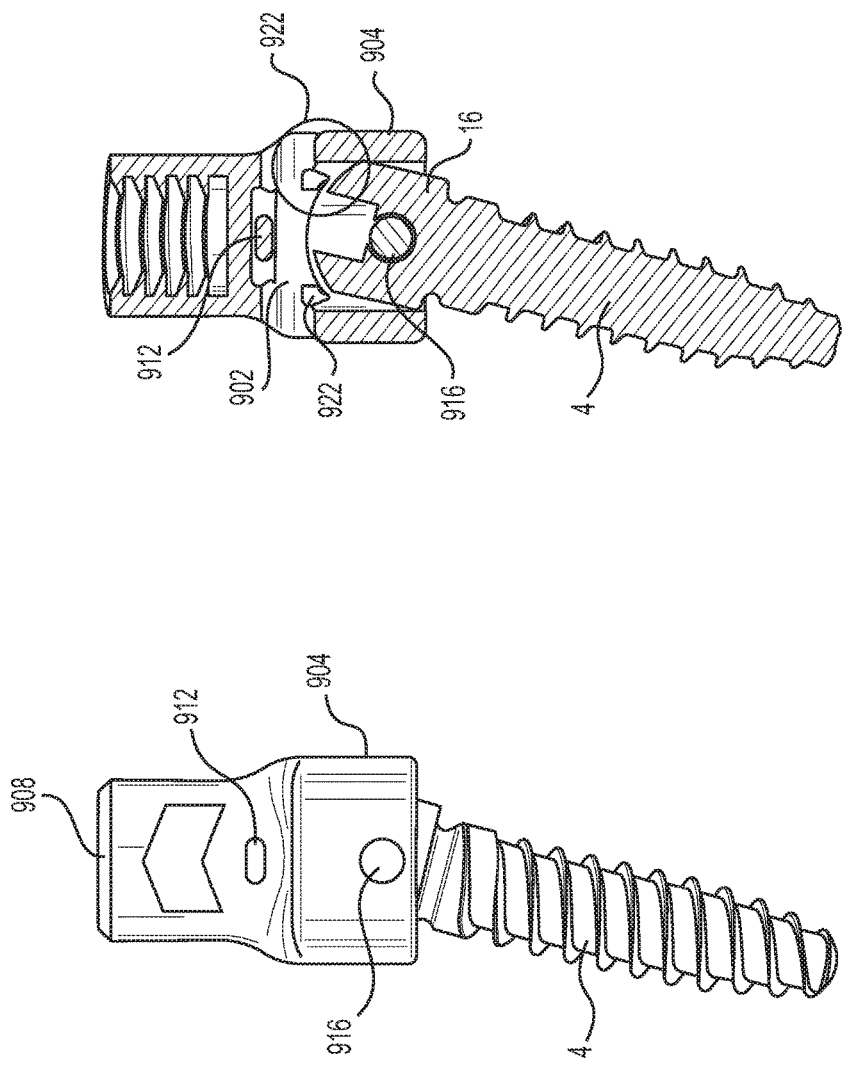

MODULAR UNIPLANAR PEDICLE SCREW ASSEMBLY FOR USE WITH A POLYAXIAL BONE FASTENER

FIELD OF THE INVENTION

The present invention relates generally to a pedicle screw assembly, and more particularly to a uniplanar tulip assembly that can be intra-operatively coupled to a polyaxial bone fastener.

BACKGROUND OF THE INVENTION

Many types of spinal irregularities such as scoliosis, kyphosis, lordosis, etc., can cause pain, limit range of motion, or injure the nervous system within the spinal column. These irregularities can result from trauma, tumor, disc degeneration, and disease. Oftentimes, these irregularities are treated by adjusting a portion of the spinal column and immobilizing that portion of the spine. This treatment involves affixing a plurality of pedicle screw assemblies (which includes a tulip element and a bone fastener) to one or more vertebrae and then connecting the pedicle screw assemblies to an elongate rod that generally extend in the direction of the axis of the spine. The connection is typically achieved by attaching the elongated rod to the tulip element of each pedicle screw assembly affixed to the vertebras.

There are many types of pedicle screw assemblies that surgeons can use to immobilize a portion of the spinal column. Such assemblies include, for example, polyaxial, monoaxial, and uniplanar pedicle screw assemblies. Each of these assemblies is characterized by whether their tulip element can be angulated relative to the bone fastener and in which plane(s) of the bone fastener.

A polyaxial pedicle screw assembly provides the greatest flexibility in tulip movement. More specifically, a tulip element of a polyaxial assembly is allowed to pivot freely in any direction and in all planes relative to a central axis of its respective bone fastener. This feature enables polyaxial assemblies more variability in rod placement.

A monoaxial pedicle screw assembly typically has a unitary construction in that the bone fastener and tulip element are machined from a single piece of biocompatible metal or plastic. This type of construction prevents the monoaxial pedicle screw assembly from being able to pivot about the bone fastener. This type of unitary construction also disallows the tulip element from being uncoupled from the bone fastener.

A uniplanar pedicle screw assembly, on the other hand, allows its tulip element to pivot back and forth in one plane about a central axis of the bone fastener, while simultaneously preventing movement of the tulip element in all other planes. This feature enables uniplanar assemblies to maintain rigidity in a particular plane during deformity correction. It should be noted, however, that uniplanar assemblies share a common property with monoaxial assemblies; that is, the tulip element of a uniplanar assembly cannot be uncoupled from the bone fastener and requires a different bone fastener head geometry to provide rigidity. This is due to the fact that the bone fastener head of a uniplanar assembly has a geometry that is different from the bone fastener head of a polyaxial assembly. The geometry for a uniplanar assembly is designed to resist angulation in one direction, but it also requires a more complex assembly process that is time consuming and dangerous in-situ.

With this knowledge, surgeons performing surgery to correct spinal irregularities will typically decide beforehand on which of the pedicle screw assemblies to affix to a pedicle of a particular vertebra. For example, a surgeon may decide beforehand to use a polyaxial pedicle screw assembly on a particular vertebral body for ease of rod placement. Based on this decision, the surgeon will affix the polyaxial assembly (which includes a tulip element and a bone fastener) as a single unit onto that vertebral body. However, after affixing the polyaxial assembly onto the vertebral body, the surgeon may determine intra-operatively that deformity correction is needed at the affected vertebral body and that a uniplanar assembly would be more suitable for this purpose.

One way to solve this problem is to replace (e.g., by unscrewing) the polyaxial assembly initially affixed to the vertebral body, and then affixing (e.g., by screwing) a uniplanar assembly into the same hole. However, this solution is time consuming because it requires multiple steps and may compromise the structural integrity of the pedicle/vertebra due to the repeated screwing and unscrewing of bone fasteners.

Because of these deficiencies in the prior art, there exists a need to provide a modular pedicle screw assembly that enables a surgeon to intra-operatively use different types of tulip assemblies without having to screw and unscrew bone fasteners.

SUMMARY OF THE INVENTION

The present invention provides a way to couple a uniplanar tulip assembly onto the same bone fastener head as a polyaxial tulip assembly without some of the deficiencies in the prior art.

In accordance with an illustrative embodiment of the present invention, provided is a modular pedicle screw assembly that allows a surgeon to install, couple, etc., a uniplanar tulip assembly onto the same bone fastener as a polyaxial tulip assembly. The uniplanar tulip assembly of the present invention comprises a longitudinal slot and an adapter arranged with a lower portion and an upper portion. The lower portion of the adapter is sized and shaped to be received in a recess arranged on the head of a polyaxial bone fastener. The upper portion (which extends from the lower portion) is adapted to slide along the longitudinal slot of the uniplanar tulip assembly; particularly, the longitudinal slot of the saddle element of the tulip assembly. This configuration: (i) allows movement of the tulip assembly in a first plane along a direction that is parallel to a longitudinal axis of the longitudinal slot and (ii) prevents movement of the tulip assembly in a second plane lateral to the first plane relative to the bone fastener. In this way, a surgeon can intra-operatively choose between a polyaxial tulip assembly and a uniplanar tulip assembly without having to screw and unscrew the bone fastener from the vertebral body, as currently performed in the prior art.

In an alternative embodiment of the present invention, provided is a tulip assembly that is adapted to constrain the polyaxial movement of the overall assembly to a uniplanar movement. The tulip assembly comprises a tulip element, a saddle element, and a clamp element. The saddle element rigidly houses the clamp element to form a locking clamp assembly, which assembly is arranged within a bore of the tulip element. The clamp element is adapted to be coupled onto the head of a bone fastener in such a way that the tulip assembly is allowed to pivot freely in all directions about a central axis of the bone fastener head. When the clamp element is compressed within the saddle element, the tulip assembly is no longer permitted to pivot freely. That is, the polyaxial movement of the tulip assembly is constrained to a uniplanar movement even though the clamp element has been compressed within the saddle element. This is due to the fact that the saddle element has two protrusions, each of which is seated within a corresponding recess (e.g., a keyhole) arranged on an inner surface of the tulip element. This configuration enables the tulip element to pivot or angulate in a first plane, while providing rigidity in a second plane lateral to the first plane.

In a further alternative embodiment of the present invention, the tulip element is coupled to a sleeve assembly that has a pair of oppositely positioned inwardly protruding pins. The pins of the sleeve assembly is adapted to prevent movement of the tulip element from pivoting about a central axis of bone fastener in a first plane, while providing rigidity in a second plane lateral to the first plane.

In a further embodiment of the present invention, the tulip element and bone fastener head are adapted to receive a translation rod to provide the tulip element with rotational and translational capabilities relative to the bone fastener.

These advantages of the present invention will be apparent from the following disclosure and the appended claims.

BRIEF DESCRIPTION OF THE DRAWINGS

FIGS. 12-14 is a cross-sectional view of the polyaxial pedicle screw assembly of FIG. 1 in accordance with the present invention.

FIG. 20 is a perspective view of the tulip, saddle, and clamp elements of the modular uniplanar tulip assembly of FIGS. 19A-19C in accordance with an alternative embodiment of the present invention.

FIG. 24A is a perspective view of a pedicle screw assembly with a translation rod in accordance with an alternative embodiment of the present invention.

FIG. 24B is a perspective view of the pedicle screw assembly of FIG. 24B disassembled in accordance with an alternative embodiment of the present invention.

FIG. 26A is a side view of the pedicle screw assembly of FIG. 24A showing rotational movement of the tulip element relative to the bone faster in accordance with an alternative embodiment of the present invention.

FIG. 26B is a cross-sectional side view of the pedicle screw assembly of FIG. 26A showing rotational movement of the tulip element relative to the bone faster in accordance with an alternative embodiment of the present invention.

DETAILED DESCRIPTION

Figure 1:
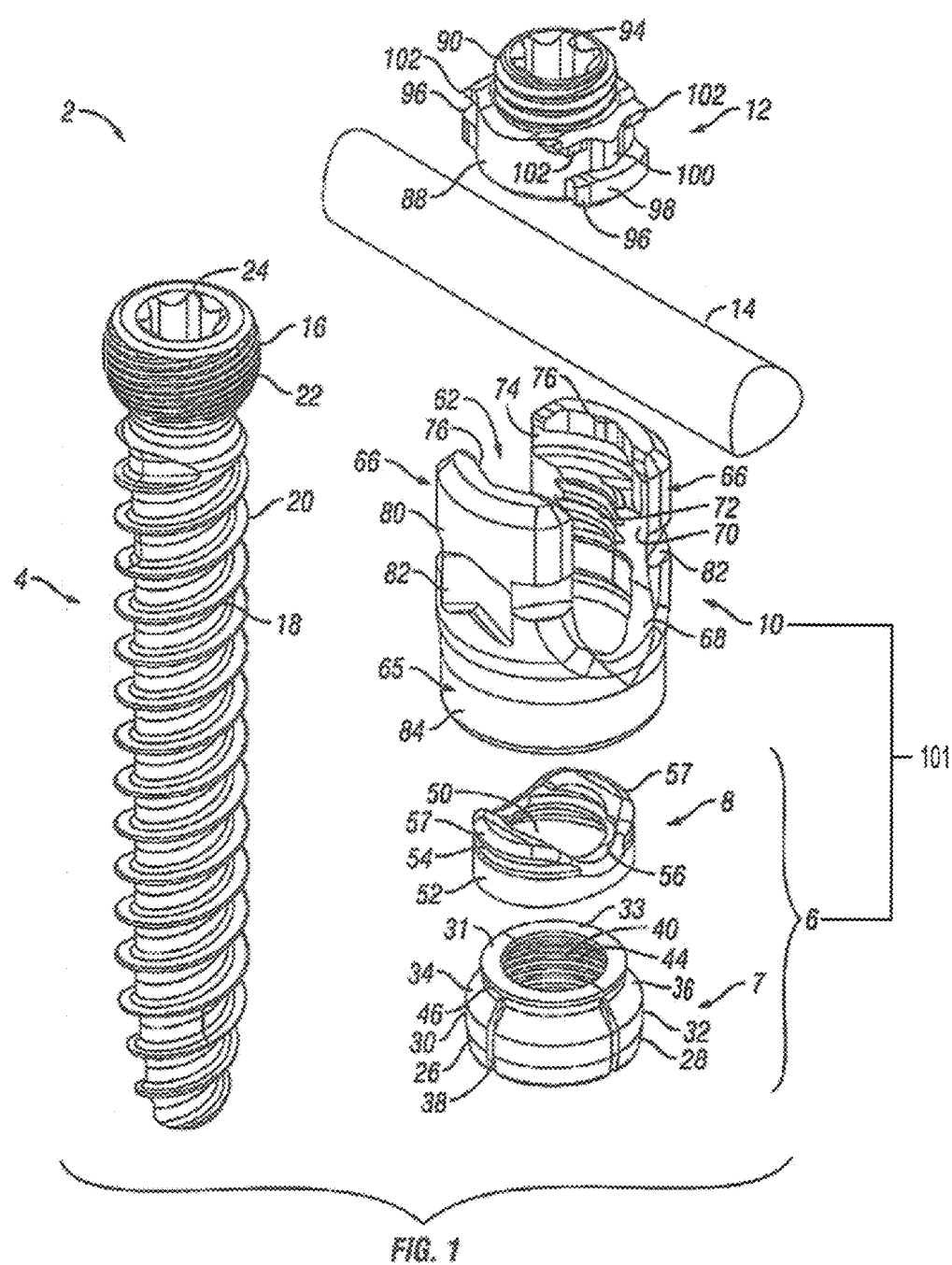
FIG. 1 is a perspective view of a polyaxial pedicle screw assembly in accordance with an illustrative embodiment of the present invention.

A Modular Uniplanar Pedicle Screw Assembly for Use with a Polyaxial Bone Fastener FIG. 1 is an exploded view of a polyaxial pedicle screw assembly 2 in accordance with an illustrative embodiment of the present invention. As illustrated, the polyaxial pedicle screw assembly 2 may comprise a polyaxial bone fastener 4, a polyaxial tulip assembly 101 having a tulip element 10 and a locking clamp assembly 6 (which may comprise, for example, a clamp element 7 and a saddle element 8), and a locking cap assembly 12. As will be discussed in more detail below, the bone fastener 4 may be loaded from the bottom of the tulip element 10 with the locking clamp assembly 6 already loaded therein. Prior to being locked into place, the tulip element 10 can be pivoted, angulated, and rotated in a plurality of positions with respect to a central axis of the bone fastener 4. Once the tulip element 10 is at the desired position with respect to the bone fastener 4, the tulip element 10 may be locked onto the bone fastener 4. In the illustrated embodiment, the locking cap assembly 12 is configured to secure a rod 14 in the tulip element 10. In one embodiment, the tulip element 10 is fixed onto the bone fastener 4 contemporaneously with securing of the rod 14 in the tulip element 10.

As illustrated by FIG. 1, the bone fastener 4 includes a head 16 and a shaft 18 that extends from the head 16. The illustrated embodiment shows the shaft 18 having a tapered shape and threads 20. Those of ordinary skill in the art will appreciate that the shaft 18 may have a number of different features, such as thread pitch, shaft diameter to thread diameter, overall shaft shape, and the like, depending, for example, on the particular application. While the head 16 may have any general shape, at least a portion of the head 16 may have a curved surface in order to allow for rotational movement or angular adjustment of the bone fastener 4 with respect to the tulip element 10. For example, at least a portion of the head 16 may be shaped to form a portion of a ball or at least a portion of a sphere. As illustrated, the head 16 may have a roughened or textured surface 22 that improves engagement with the clamp element 7. In certain embodiments, the head 16 may have a tool engagement surface, for example, that can be engaged by a screw-driving tool or other device. The tool engagement surface can permit the physician to apply torsional or axial forces to the bone fastener 4 to drive the bone fastener 4 into the bone. In the illustrated embodiment, the tool engagement surface of the head 16 has a polygonal recess 24. For instance, the polygonal recess 24 may be a torx-shaped recess or a hexagonal recess that receives a hexagonal tool, such as an allen wrench, for example. The present invention is intended to encompass tool engagement surfaces having other shapes as well.

Figure 2:
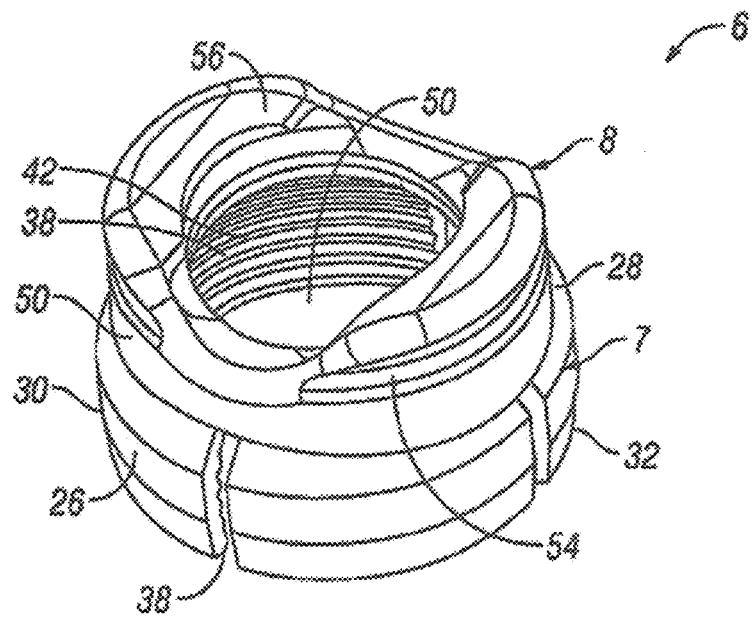
FIG. 2 is a perspective view of a locking clamp assembly for the polyaxial pedicle screw of FIG. 1 in accordance with the present invention.
Figure 3:
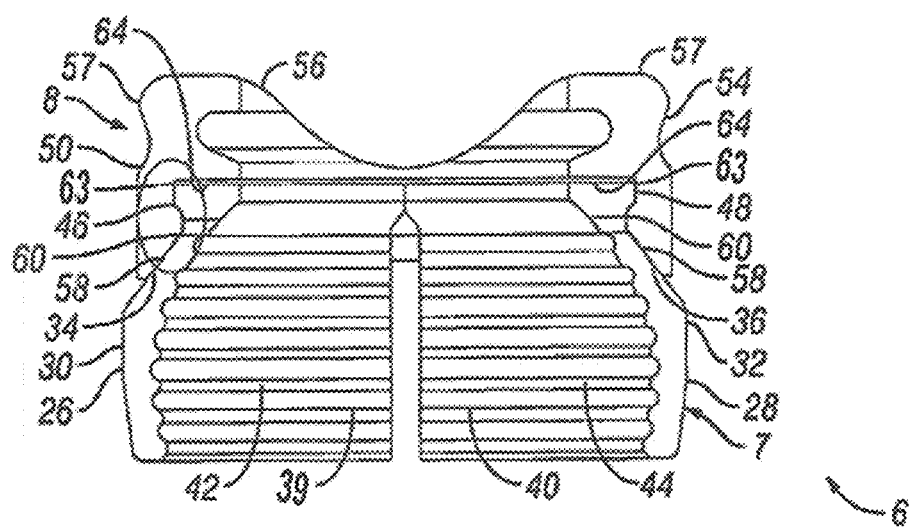
FIG. 3 is a cross-sectional view of the locking clamp assembly of FIG. 2 in accordance with the present invention.

Referring now to FIGS. 1-3, clamp element 7 of the locking clamp assembly 6 will be described in more detail in accordance with embodiments of the present invention. As illustrated, the clamp element 7 includes a first clamp portion 26 and a second clamp portion 28. In the illustrated embodiment, the first clamp portion 26 is substantially identical to and a mirror image of, the second clamp portion 28. The first and second clamp portions 26, 28 provide a collar about the head 16 of the bone fastener 4, when installed, as discussed in more detail below. The first and second clamp portions 26, 28 grip bone fastener 4 when force is applied onto the clamp element 7 by the tulip element 10. While the embodiments that are described and illustrated generally describe the first and second clamp portions 26, 28 as substantially identical, the portions 26, 28 may be of varying size and are not required to be mirror images of one another. In addition, while the clamp element 7 is illustrated as having two clamp portions (i.e., the first and second clamp portions 26, 28), the clamp element 7 may comprise more than two portions for gripping the bone fastener 4.

As illustrated, each of the first and second clamp portions 26, 28 includes an outer surface 30, 32, which may be curved or rounded, as best shown in FIGS. 1 and 2. The outer surfaces 30, 32 of the first and second clamp portions 26, 28 may each include an outer tapered surface 34, 36. In addition, the outer surfaces 30, 32 may each also have at least one slit 38 formed therein. The at least one slit 38 may, for example, allow the first and second clamp portions 26, 28 to constrict and securely engage the head 16 of the bone fastener 4. The outer surfaces 30, 32 should abut and engage the inner wedge surface 86 of the tulip element 10 of FIG. 6 when fully installed and locked in place in the tulip element 10 in accordance with present embodiments. With particular reference to FIG. 3, the first and second clamp portions 26, 28 each include inner surfaces 39, 40. When fully installed and locked in place in the tulip element 10, the inner surfaces 39, 40 should abut and engage the head 16 of the bone fastener 4 in accordance with present embodiments. The illustrated embodiment shows the inner surfaces 39, 40 having roughened or textured features 42, 44 that improve engagement with the head 16 of the bone fastener 4. The first and second clamp portions 26, 28 each may also include an external lip 46, 48, which may be located above the outer tapered surfaces 34, 36, as best seen in FIG. 3. The first and second clamp portions 26, 28 each may also include an upper surface 31, 33, as best seen in FIG. 1.

Figure 4:
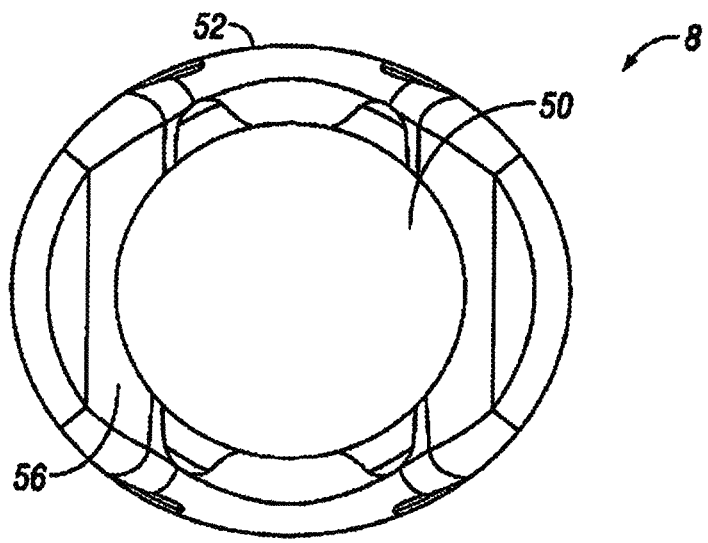
FIG. 4 is a top view of a saddle element for the polyaxial pedicle screw of FIG. 1 in accordance with the present invention.
Figure 5:
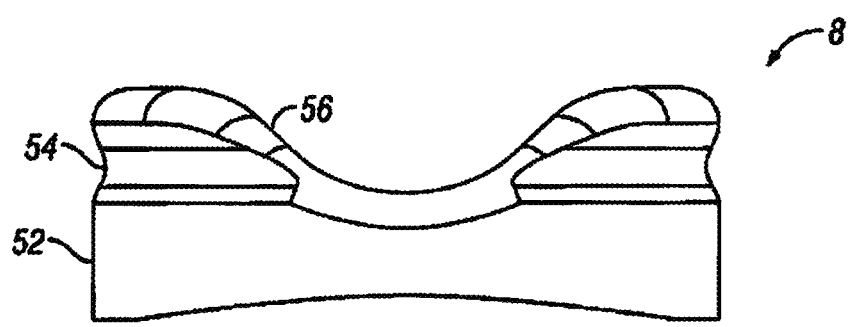
FIG. 5 is a side view of the saddle element of FIG. 4 in accordance with the present invention.

Referring now to FIGS. 1-5, the saddle element 8 of the locking clamp assembly 6 will be described in more detail in accordance with embodiments of the present invention. As illustrated, the saddle element 8 may include a bore 50. The lower portion of the bore 50 may be sized to receive the upper portion of the clamp element 7, including external lips 46, 48 of the first and second clamp portions 26, 28. The body of the saddle element 8 includes an outer surface 52 having a recessed portion 54. The outer surface 52 may be generally rounded, for example. As best seen in FIG. 4, the outer surface 52 of the saddle element 8 may be generally elliptical, in one embodiment. The elliptical shape of the outer surface 52 should, for example, limit radial motion of the saddle element when installed in the tulip element 10. The elliptical shape of the outer surface 52 should, for example, limit radial motion of the saddle element 8 when installed in the tulip element 10. The saddle element 8 further may include an upper surface 56. In the illustrated embodiment, the upper surface 56 defines a seat that receives the rod 14. As illustrated, the upper surface 56 may be generally convex in shape. In the illustrated embodiment, the saddle element 8 further includes an upper lip 57.

With particular reference to FIG. 3, the saddle element 8 further includes an inner wedge surface 58. As illustrated, the inner wedge surface 58 may be disposed around a lower portion of the body of the saddle element 8. In one embodiment, the inner wedge surface 58 forms a conical wedge. The inner wedge surface 58 operates, for example, to engage the outer tapered surfaces 34, 36 of the first and second clamp portions 26, 28 to force the clamp element 7 down the bore 62 of the tulip element 10. The saddle element 8 further may include an inner protruding surface 60 adjacent to the inner wedge surface 58 and an inner recessed surface 63 adjacent the inner protruding surface 60. The saddle element 8 further may include an inner seat 64. As illustrated, the inner seat 64 may be downwardly facing for receiving upper surfaces 31, 33 of the first and second clamp portions 26, 28.

In accordance with present embodiments, the locking clamp assembly 6 can be assembled prior to insertion into the tulip element 10. In one embodiment, for assembly, the clamp element 7 may be inserted into the saddle element 8 upwardly through the opening of the body of the saddle element 8. The outer surfaces 30, 32 of the first and second clamp portions 26, 28 should slidingly engage the inner wedge surface 58 of the saddle element 8 as the clamp element 7 is inserted. The clamp element 7 should be inserted until the external lips 46, 48 of the first and second clamp portions 26, 28 pass the inner protruding surface 60 of the saddle element 8. The inner protruding surface 60 engages the external lips 46, 48 to secure the clamp element 7 in the saddle element 8. In the illustrated embodiment, the locking clamp assembly 6 will not fit downwardly through the top of the bore 62 of the tulip element 10 as the locking clamp assembly has an outer diameter at its biggest point that is larger than the inner diameter of the upper portion of the bore 62.

Figure 6:
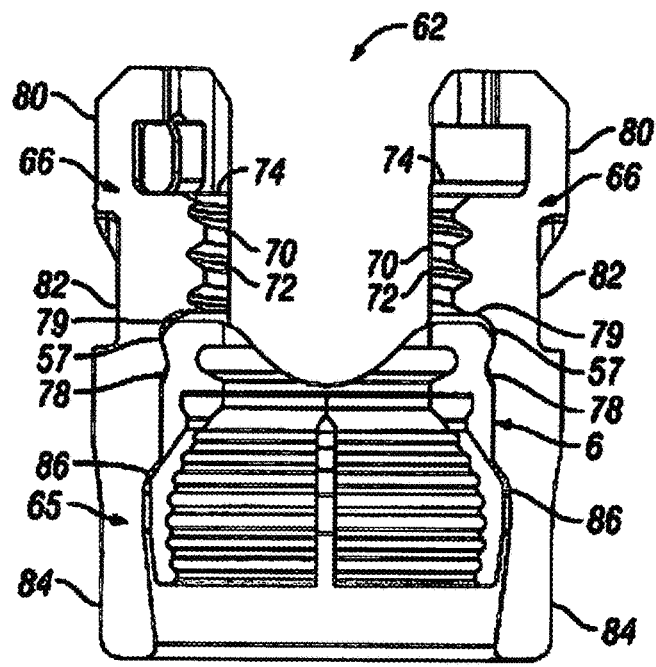
FIG. 6 is a cross-sectional view of the locking clamp assembly of FIG. 2 disposed in a tulip element in an unlocked configuration in accordance with the present invention.
Figure 9:
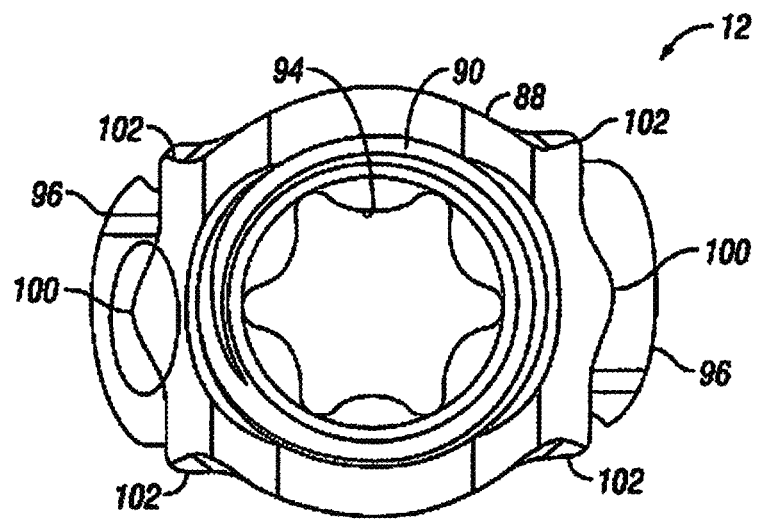
FIG. 9 is a top view of a locking cap assembly in accordance with the present invention.
Figure 8:
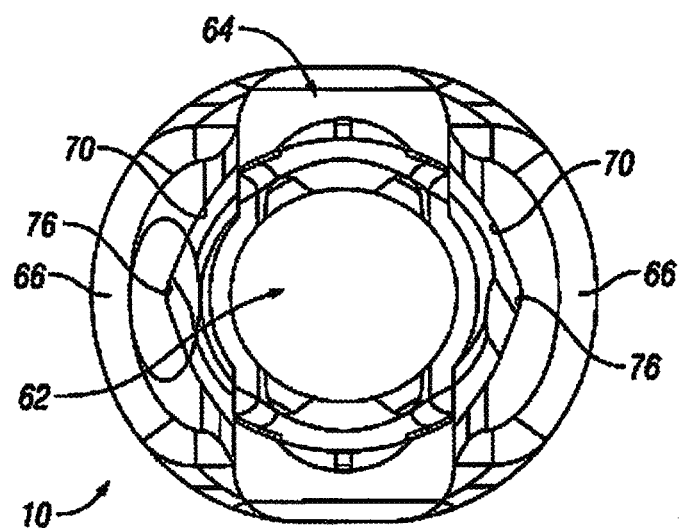
FIG. 8 is a top view of a tulip element depicted in FIGS. 6 and 7 in accordance with the present invention.
Figure 10:
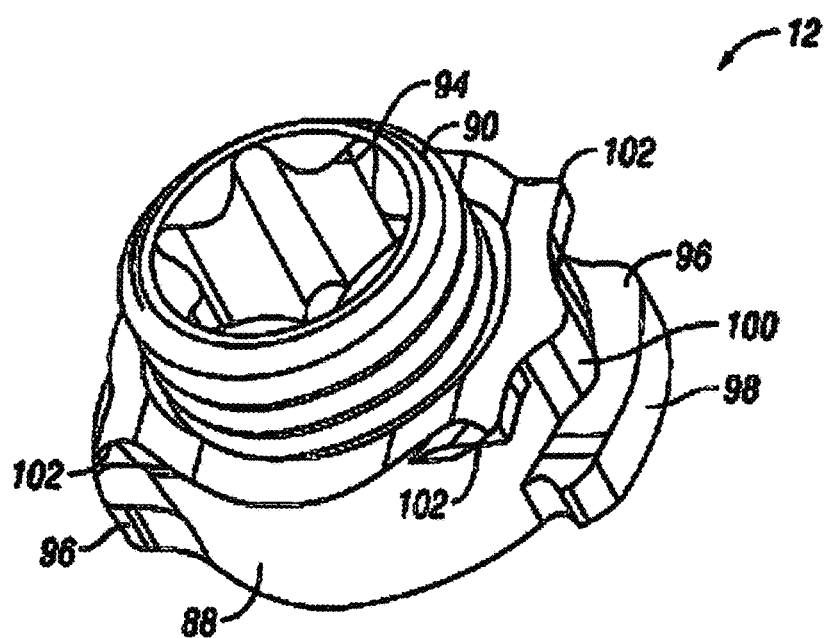
FIG. 10 is a perspective view of the locking cap assembly depicted in FIG. 9 in accordance with the present invention.
Figure 11:
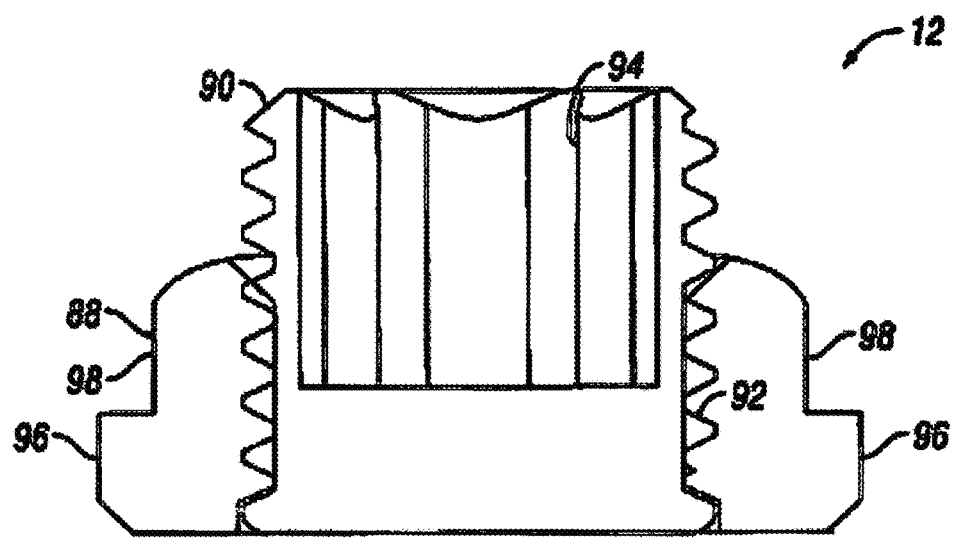
FIG. 11 is a cross-sectional view of the locking cap assembly of FIG. 10 in accordance with the present invention.

Referring now to FIGS. 1 and 6-8, the tulip element 10 will be described in more detail in accordance with embodiments of the present invention. As illustrated, the tulip element 10 may comprise bore 62, a body 65 and a pair of oppositely positioned lateral arms 66 that extend upwardly from the body 65. In the illustrated embodiment, the arms 66 define a U-shaped channel 68 sized to receive the rod 14. Each of the arms 66 has an interior surface 70 having a threaded portion 72 for engaging corresponding threads on a screw-driving tool. The interior surface 70 of each of the arms 66 further may include a slot 74 for receiving corresponding tabs 96 (e.g., FIG. 9) of the locking cap assembly 12 and a recessed surface 76 for engaging corresponding protuberances 100 (e.g., FIG. 9) of the locking cap assembly 12. As illustrated, the recessed surface 76 of each of the arms 66 may be located above the slot 74. The interior surface 70 of each of the arms 66 further may include a protuberance 78, as best seen in FIG. 6. In the illustrated embodiment, the protuberance 78 of each of the arms 66 is located below the threaded portion 72 with the threaded portion 72 being located between the protuberance 78 and the slot 74. As best seen in FIG. 6, the interior surface 70 of each of the arms 66 further may form a downwardly facing seat 79, for example, which may limit or restrict movement of the locking clamp assembly 6 through the bore 62. In some embodiments, saddle element 8 has a pair of oppositely positioned projections, with each projection extending laterally outwardly from the outer surface 52. Each projection is adapted to be received in a corresponding recess arranged in the interior surface of the tulip element 10. The recess is sized and shaped to complement the size and shape of the projections in order to limit radial motion of the saddle element 8 when installed in the tulip element. Continuing with the illustrative embodiment of the present invention, as each of the arms 66 further may include an outer surface 80. The outer surface 80 of each of the arms 66 may include a tool engagement groove 82 formed on the outer surface 80, which may be used for holding the tulip element 10 with a suitable tool (not illustrated).

Figure 7:
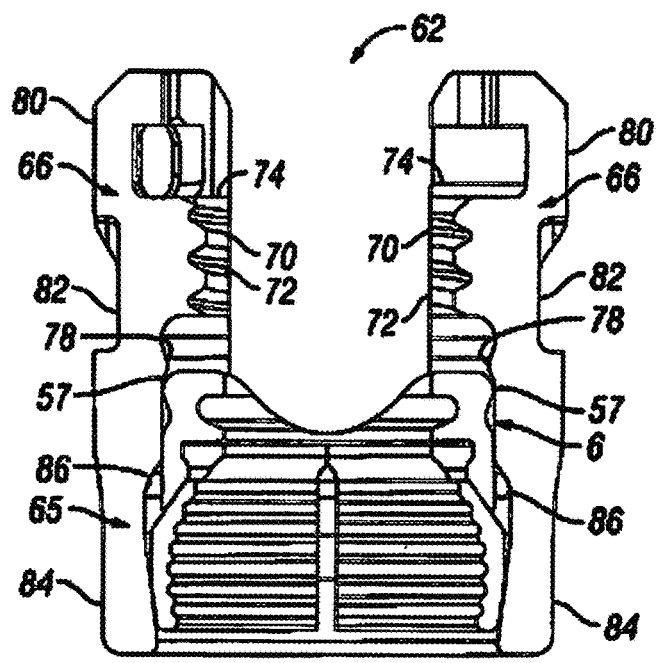
FIG. 7 is a cross-sectional view of the locking clamp assembly of FIG. 2 disposed in a tulip element in a locked configuration in accordance with the present invention.

As illustrated, the body 65 of the tulip element 10 may have an outer surface 84, which may be curved or rounded, as best seen in FIG. 1. With particular reference to FIGS. 6 and 7, the body 65 further may include an inner wedge surface 86 disposed around a lower portion of the bore 62. In one embodiment, the inner wedge surface 86 forms a conical wedge. The inner wedge surface 86 of the body 65 of the tulip element 10, for example, may abut and engage the outer surfaces 30, 32 of the first and second clamp portions 26, 28 when the locking clamp assembly 6 is fully installed and locked in place.

In accordance with present embodiments, the locking clamp assembly 6 may be installed in the tulip element 10 in either an unlocked position or a locked position. FIG. 6 illustrates the locking clamp assembly 6 disposed in the tulip element 10 in the unlocked position in accordance with embodiments of the present invention. In FIG. 6, the locking clamp assembly 6 has been inserted into the tulip element 10 upwardly through the bore 62. The locking assembly 6 should be inserted until the upper lip 57 of the saddle element 8 passes the protuberances 78 located on the interior surfaces 70 of the arms 66 of the tulip element 10. The protuberances 78 should engage the upper lip 57 to secure the locking clamp assembly 6 in the tulip element 10. While not illustrated on FIG. 6, the bone fastener 4 (e.g., shown on FIG. 1) can now be placed into the locking assembly 6 through a snap fit engagement with the clamp element 7. There should be sufficient clearance for the clamp element 7 to expand and snap around the head 16 of the bone fastener 4. The locking clamp assembly 6 and the tulip element 10, however, should still be free to pivot and rotate with respect to a central axis of the bone fastener 4. The tulip element 10 can be moved and rotated to obtain a desired portion with respect to the bone fastener 4. The locking clamp assembly 6 should also move with the tulip element 10 during rotation of the tulip element 10 with respect to the bone fastener 4. Once the tulip element 10 is at the desired position, the tulip element 10 may be locked onto the bone fastener 4. The locking clamp assembly 6 and the tulip element 10 should cooperate to lock the clamp assembly 6 onto the head 16 of the bone fastener 4.

FIG. 7 illustrates the locking clamp assembly 6 disposed in the tulip element 10 in the locked position in accordance with embodiments of the present invention. In FIG. 7, the locking clamp assembly 6 has been pushed downwardly in the bore 62 of the tulip element 10. As illustrated, the locking clamp assembly 6 has been pushed downward until the upper lip 57 of the saddle element 8 passes the protuberances 78 located on the interior surfaces 70 of the arms 66 of the tulip element 10. As the locking clamp assembly 6 moves downward, the clamp element 7 engages the body 65 of the tulip element 10. As illustrated, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4 (e.g., FIG. 1). In the locked position, tulip element 10 should be locked onto the bone fastener 4, thus preventing further positioning of the tulip element 10 with respect to the bone fastener 4.

Referring now to FIGS. 1 and 9-11, the locking cap assembly 12 will be described in more detail in accordance with embodiments of the present invention. As illustrated, the locking cap assembly 12 may comprise a body 88 and a set screw 90 threaded into a bore 92 in the body 88. The set screw 90 may have a length, for example, that is longer than the length of the bore 92. In the illustrated embodiment, at least a portion of the set screw 90 extends from the top of the body 88. In certain embodiments, the set screw 90 may have a tool engagement surface, for example, that can be engaged by a screw-driving tool or other device. The tool engagement surface can permit the physician to apply torsional or axial forces to the set screw 90 to advance the set screw 90 through the body 88 and onto the rod 14. When the locking cap assembly 12 is in its locked position, the set screw 90 can be advanced through the body 88 to engage the rod 14, applying downward force onto the rod 14 and securing it to the tulip element 12. In one embodiment, the set screw 90 forces the rod 14 downward and into contact with the locking clamp assembly 6 causing the locking cap assembly 6 to move downward in the tulip element 10. In the illustrated embodiment, the tool engagement surface of the set screw 90 is a polygonal recess 94. For instance, the polygonal recess 94 may be a hexagonal recess that receives a hexagonal tool, such as an allen wrench, for example. The present invention is intended to encompass tool engagement surfaces having other shapes, such as slot or cross that may be used, for example, with other types of screwdrivers. In an alternative embodiment (not illustrated), the engagement surface may be configured with a protruding engagement surface that may engage with a tool or device having a corresponding recess.

In accordance with present embodiments, the body 88 may have one or more projections. For example, the body 88 may comprise lower tabs 96 projecting radially from a lower end of the body 88. In the illustrated embodiment, the body 88 comprises a pair of lower tabs 96 located on opposite sides of the body 88. As illustrated, the lower tabs 96 may each have an outer surface 98 that is generally rounded in shape. In addition, while the body 88 is illustrated as having two lower tabs 96, the body 88 may comprise more than two lower tabs 96. As illustrated, the body 88 further may comprise protuberances 100. The protuberances 100 may engage with corresponding recessed surface 76 of the arms 66 of the tulip element 10. The protuberances 100 may be capable of providing a tactile or audible signal to the physician, such as a click that may be felt or heard, when the locking cap assembly 12 has reached its locking position. The protuberances 100 also may assist in maintaining the locking cap assembly 12 in its locked position. In the illustrated embodiment, the body 88 further may comprise tool engagement features. The tool engagement features may, for example, be used for holding or manipulating the locking cap assembly 12 with a suitable tool (not illustrated). In the illustrated embodiment, the locking cap assembly 12 includes upper tabs 102. As illustrated, the tabs 102 may be formed at the upper surface of the body 88. In the illustrated embodiment, the locking cap assembly 12 includes four upper tabs 102 at the corners of the upper surface. In addition, while the body 88 is illustrated as having four upper tabs 102, the body 88 may comprise more or less than four upper tabs 102.

To place the locking cap assembly 12 onto the tulip element 10, the lower tabs 96 should be aligned with the U-shaped channel 68 formed by the arms 66 of tulip element 10 and the locking cap assembly 12 can then be lowered downward into the bore 62 in the tulip element 10. Once the lower tabs 96 are aligned with the corresponding slots 74 in the arms 66 of the tulip element 10, the locking cap assembly 12 can be rotated. The slots 74 allow the lower tabs 96 to pass through the arms 66 when the lower tabs 96 and the slots 74 are aligned. The length of the slots 74 generally correspond to the amount of rotation needed to move the locking cap assembly 12 into or out of a locked position. In one embodiment, the locking cap assembly 12 rotates from about 60° to about 120° for placement into a locking positions, alternatively, about 80° to about 100°, and, alternatively, about 90°. As previously mentioned, the protuberances 100 can be configured to provide a tactile or audible signal to the physician when the locking cap assembly 12 has reached its locked assembly. In addition, the protuberances 100 can also assist in maintaining the locking cap assembly 12 in its locked position. Other features such as undercuts and geometric mating surfaces may be used to prevent rotation in the opposite direction. With the locking cap assembly 12 locked in place, the set screw 94 can then be rotated. As the set screw 94 moves downward and extends from the bottom of the base 88 of the locking cap assembly 12, the set screw 94 presses against the rod 14 securing it in the tulip element 10. In addition, the rod 14 may also be pressed downward into engagement with the locking clamp assembly 6 forcing it downward in the tulip element 10. As the locking clamp assembly 6 moves downward, the clamp element 7 engages the body 65 of the tulip element 10. As best seen in FIG. 7, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4 and secure it with respect to the tulip element 10.

Referring now to FIGS. 12-14, locking of the tulip element 10 onto the bone fastener 4 is illustrated in more detail in accordance with embodiments of the present invention. For the purposes of this illustration, the locking cap element 12 is not shown. The tulip element 10 shown in FIGS. 12-14 is similar to the tulip element 10 described previously except that the tulip element 10 does not include a threaded portion 72 (e.g., FIGS. 6-7) or a downwardly facing seat 79 (e.g., FIG. 6) in the interior surface 70 of the arms 66 of the tulip element 10. FIG. 12 illustrates the locking clamp assembly 6 installed in the tulip element 10 in an unlocked position. As previously mentioned, the locking clamp assembly 6 can be inserted into the tulip element 10 upwardly through the bore 62. As shown in FIG. 12, the locking assembly 6 should be inserted until the upper lip 57 of the saddle element 8 passes the protuberances 78 located on the interior surfaces 70 of the tulip element 10. The protuberances 78 should engage the upper lip 57 to secure the locking clamp assembly 6 in the tulip element 10. As illustrated by FIG. 13, the bone fastener 4 can now be placed into the locking assembly 6 through a snap fit with the clamp element 7. There should be sufficient clearance for the clamp element 7 to expand and snap around the head 16 of the bone fastener 4. The locking clamp assembly 6 and the tulip element 10, however, should still be free to pivot and rotate with respect to the bone fastener 4. The tulip element 10 can be pivoted and rotated to obtain a desired portion with respect to the bone fastener 4. Once the tulip element 10 is at the desired position, the tulip element 10 may be locked onto the bone fastener 4. The locking clamp assembly 6 and the tulip element 10 should cooperate to lock the clamp assembly 6 onto the head 16 of the bone fastener 4.

FIG. 14 illustrates the locking clamp assembly 6 disposed in the tulip element 10 in the locked position and clamping onto the head 16 of the bone fastener 4 to secure the bone fastener 4 with respect to the tulip element 10 in accordance with embodiments of the present invention. As seen in FIG. 14, the locking clamp assembly 6 has been pushed downwardly in the bore 62 of the tulip element 10 until the upper lip 57 of the saddle element 8 passes the protuberances 78 located on the interior surfaces 70 of the arms 66 of the tulip element 10. As the locking clamp assembly 6 moves downward, the clamp element 7 engages the body 65 of the tulip element 10 such that the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4. In the locked position, tulip element 10 should be locked onto the bone fastener 4, thus preventing further positioning of the tulip element 10 with respect to the bone fastener 4.

During a surgical procedure, the polyaxial tulip assembly 101 is coupled to the polyaxial head 16 of the bone fastener 4, as shown in FIG. 12. With a driving tool, the surgeon can insert the bone fastener 4 (with the tulip assembly 101 coupled to the head 16) into a pedicle or vertebral body located at a particular region of a spinal column. However, as discussed at the beginning of this disclosure, the surgeon may intra-operatively determine after the bone fastener 4 has been inserted into the pedicle or vertebral body that deformity correction is needed at this particular region of the spinal column.

In accordance with the illustrative embodiment, the surgeon can uncouple, detach, etc., the polyaxial tulip assembly 101 from the bone fastener head 16 and then couple, install, etc., the uniplanar tulip assembly 551 onto the same bone fastener head 16. As will be appreciated from the description below, the adapter 502 when used in conjunction with the uniplanar tulip assembly 551 will allow it to pivot or angulate in a single plane relative to the polyaxial bone fastener head 16, while simultaneously preventing movement of the tulip assembly 551 in all other directions and planes of the bone fastener head 16. These features of the present invention will be described in more detail below, with respect to FIGS. 15-18D.

Figure 15:
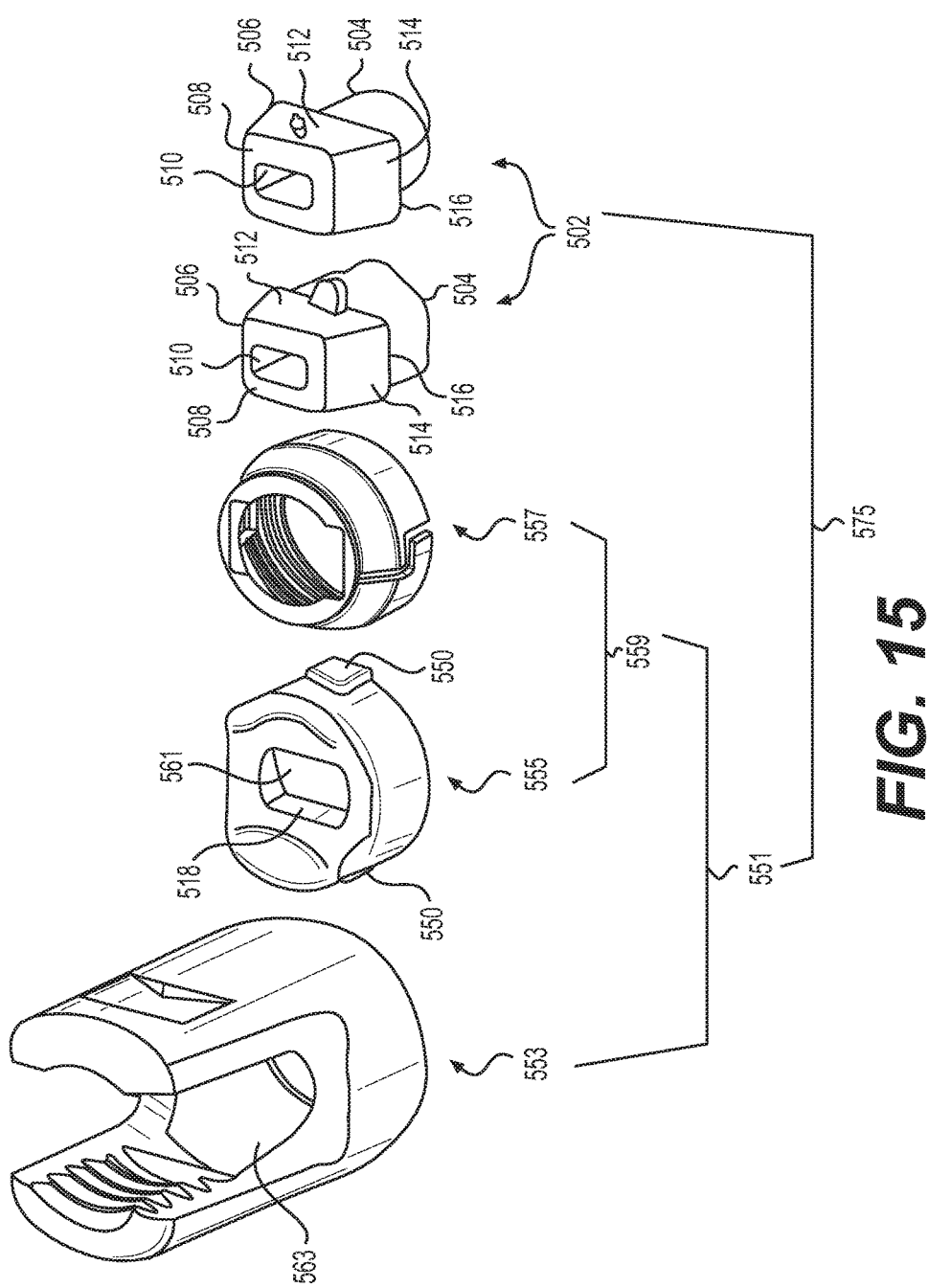
FIG. 15 is a perspective view of a modular uniplanar pedicle screw assembly having a uniplanar tulip assembly and adapter in accordance with the present invention.

FIG. 15 depicts a uniplanar tulip assembly 551, which includes tulip element 553 and locking clamp assembly 559 (i.e., clamp element 557 and saddle element 555). It will be clear to those skilled in the art, after reading this disclosure, that the tulip element 553 and the locking clamp assembly 559 are coupled or assembled together in the same or similar fashion as the polyaxial tulip assembly 101 and locking clamp assembly 6 discussed above, with respect to FIGS. 1-14. One difference, however, is that the uniplanar saddle element 555 has a longitudinal slot 561 and a pair of oppositely positioned lateral protrusions 550, each of which is not present in the polyaxial saddle element 8. Each of the lateral protrusions 550 of the uniplanar saddle elements 555 is sized and shaped to be received in a corresponding recess 563 arranged on an inner surface of the tulip element 553. Once received, saddle element 555 is prevented from rotating within the tulip element 553. It should also be noted that the uniplanar tulip assembly 551 is adapted to be coupled, installed, etc., onto the bone fastener head 16 in the same or similar fashion as the polyaxial tulip assembly 101 discussed above, with respect to FIGS. 1-14.

Figure 16:
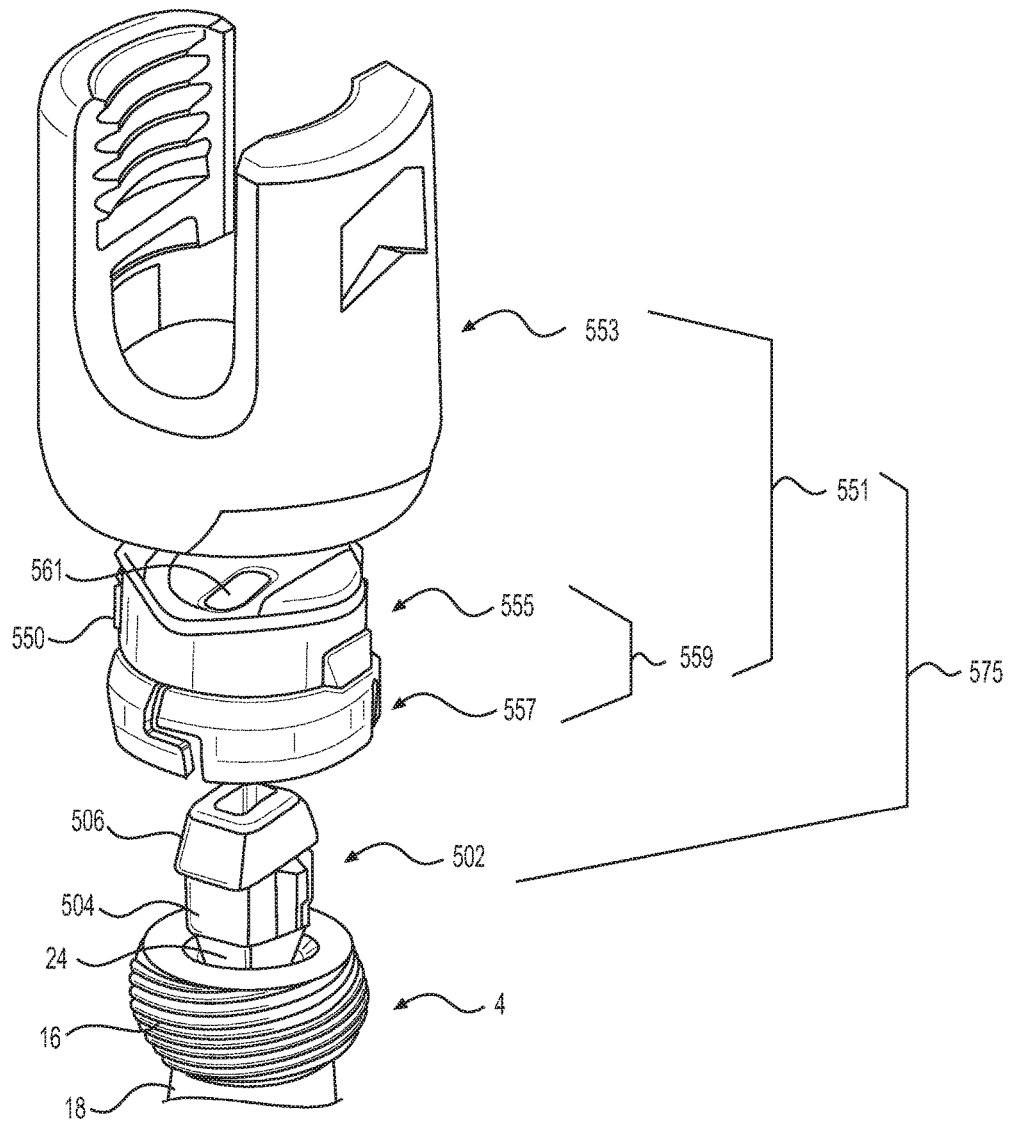
FIG. 16 is a perspective view of installing the modular uniplanar pedicle screw assembly of FIG. 15 onto the bone fastener head of the polyaxial pedicle screw assembly of FIG. 1 in accordance with the present invention.

FIG. 15 further depicts two adapters 502, with each adapter having a different shaped lower portion 504. The combination of the tulip assembly 551 and the adaptor 502 form a modular uniplanar pedicle screw assembly 575 in accordance with the present invention. As shown in the figure, the adapter 502 has a lower portion 504 and an upper portion 506 formed as a single, unitary construction. In alternative embodiments, the lower and upper portions can be two separate parts that are coupled together to form the adapter 502. In accordance with the illustrative embodiment, the lower portion 504 of the adapter 502 is sized and shaped to be received in the recess 24 of the polyaxial bone fastener head 16. In one embodiment, the lower portion 504 has a shape that complements the shape of recess 24, in order to prevent the adaptor 502 from being able to rotate about a central axis of the bone fastener head 16. This complementary shape of the lower portion and recess is shown in FIG. 16. The lower portion 504 and recess 24 can have any shape (e.g., torx-shaped, hexagonal-shaped, polygonal-shaped, etc.), as long as the shape is able to prevent the lower portion 504 from being able to rotate in the recess 24. As will be described in more detail below, combining this physical relationship with that of the upper portion 506 and the longitudinal slot 561 will enable the uniplanar tulip assembly 551 to pivot in a single plane, while simultaneously preventing movement of the tulip assembly 551 in all other directions and planes of the bone fastener 4.

Returning back to FIG. 15, this figure further illustrates the upper portion 506 of the adapter 502 extending from the lower portion 504. The upper portion 506 is defined by an upper surface 508 having a recess or hole 510, a pair of oppositely positioned lateral surfaces 512, and a pair of oppositely positioned inclined surfaces 514. Although FIG. 15 only depicts one lateral surface and one inclined surface, it should be noted that one half of the adapter 502 (when divided into equal halves) is substantially identical to and a mirror image of the other half of adapter 502. Continuing with FIG. 15, it is shown that each of the oppositely positioned inclined surfaces 514 form a flange 516, with each flange having an underside that will rests on top of the polyaxial bone fastener head 16.

To allow the uniplanar tulip assembly 551 to pivot or angulate about the polyaxial bone fastener head 16, the upper portion 506 is adapted to be received in the longitudinal slot 561 of the saddle element 555. As shown in FIG. 17A, the width of the upper portion 506 is slightly smaller than the width of the longitudinal slot 561 of the saddle element 555. That is, the upper portion 506 is sized and shaped in such a way that each of the lateral surfaces 512 of the adapter abuts against respective oppositely positioned inner walls 518 of the longitudinal slot 561. This prevents the uniplanar tulip assembly 551 from pivoting or angulating in a direction and plane that is perpendicular to the longitudinal slot 561. As further shown in FIG. 17A, the upper portion 506 once inserted into the longitudinal slot 561 does not extend past the upper surface of the pair of oppositely positioned inner walls 518 of the longitudinal slot 561. In alternative embodiments, however, the upper portion 506 may extend past the upper surface of the pair of oppositely positioned inner walls 518. Although FIG. 15 only depicts one inner wall 518, it will be appreciated by those skilled in the art that one half of the saddle element 555 (when divided into equal halves) is substantially identical to and a mirror image of the other half of the saddle element.

Figure 17C:
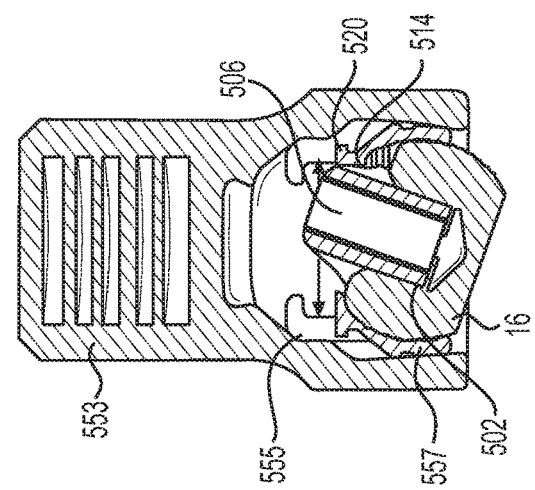
FIG. 17C is a cross-sectional side view of the adapter sliding along the longitudinal slot of the saddle element in accordance with the present invention.
Figure 17B:
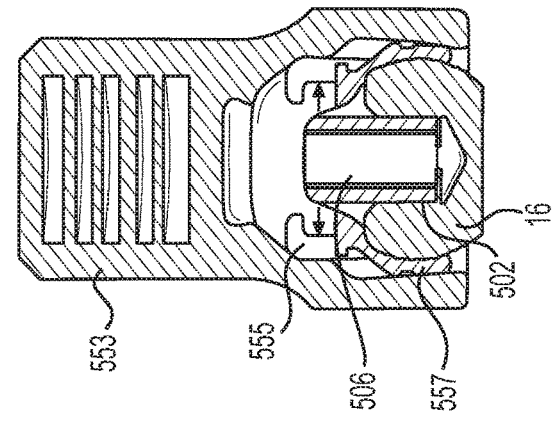
FIG. 17B is a cross-sectional side view of the adapter inserted into the recess of the bone fastener and the longitudinal slot of the saddle element in accordance with the present invention.
Figure 17A:
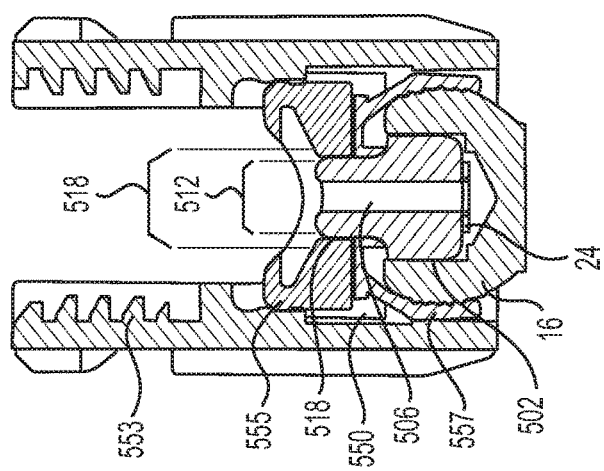
FIG. 17A is a cross-sectional front view of the adapter inserted into the recess of the bone fastener and the longitudinal slot of the saddle element in accordance with the present invention.

From the physical relationship of the elements discussed above, the upper portion 506 is adapted to slide along the longitudinal slot 561 of the uniplanar tulip assembly 551 (i.e., along the longitudinal slot of the saddle element 555 and in the direction of the arrows illustrated in FIGS. 17B and 17C) to allow movement of the tulip assembly 551 (which includes the tulip element 553, clamp element 557, and saddle element 555) in a first plane along a direction that is parallel to a longitudinal axis of the longitudinal slot 561. When sliding along the longitudinal slot, the pair of oppositely positioned inclined surfaces 514 abut against respective oppositely positioned inner walls 520 of the tulip assembly 551 (e.g., the inner wall of the clamp element 557, saddle element 555, or combination thereof) to stop the upper portion 506 from sliding past a predefined location along the longitudinal slot 561. The physical relationship of the lower and upper portions also prevents any sort of pivoting or angular movement of the uniplanar tulip assembly 551 in a second plane lateral to the first plane relative to the bone fastener 4, thereby providing rigidity in the second plane so that a surgeon can adjust (e.g., straighten-out, undeform, etc.) a particular region of a patient's spinal column that is suffering from scoliosis or other spinal deformities.

In accordance with the illustrative embodiment, the direction parallel to the longitudinal axis of the longitudinal slot 561 in the first plane is the cephalad-caudal direction of a body (i.e., the direction from head to toe), while the second plane lateral to the first plane is the medial-lateral direction of the body (i.e., the direction from the midline of the body to the side).

As discussed above, alternative embodiments of the present invention enable the adapter 502 to rotate about a central axis of the polyaxial bone fastener head 16 to change the plane in which the uniplanar tulip assembly 551 can pivot or angulate. To achieve this, the lower portion 504 has a cylindrical shape, instead of a shape that prevents the lower portion 504 from rotating while in the recess 24, as discussed above. The cylindrical shape of the lower portion 504 is shown in FIG. 15. When the cylindrical lower portion 504 is used in combination with the upper portion 506, this combination enables the uniplanar tulip assembly 551 (even when clamped onto the bone fastener head 16) to rotate about a central axis of the head 16. In this way, the surgeon can intra-operatively change the plane in which the tulip assembly 551 pivots or angulates.

For example, the uniplanar tulip assembly 551 including the adapter 502 is clamped onto the polyaxial bone fastener head 16. The surgeon would like to intra-operatively change the pivot or angulation plane of the tulip assembly 551 from the cephalad-caudal section to the medial-lateral section of the body. The surgeon can achieve this by rotating the tulip assembly 90° while the tulip assembly 551 is clamped onto the bone fastener head 16. Because the upper portion 512 of the adapter 502 is arranged within the tulip assembly 551 in the manner discussed above, rotating the tulip assembly 90° will also rotate the adapter 90°. Once rotated, the uniplanar tulip assembly 551 can now pivot or angulate about a central axis of the polyaxial bone faster head 16 in the medial-lateral direction, while preventing movement in the cephalad-caudal direction.

It should be clear to those skilled in the art, after reading this disclosure, that the tulip assembly 551 (when employing the adapter 502 with a cylindrical lower portion 504) can be rotated in any number of degrees to change the direction/plane in which the tulip assembly 551 may pivot and prevent movement. In alternative embodiments of the present invention, the longitudinal slot 561 may be oriented perpendicular to the orientation shown in the illustrative embodiment, or at another angle. This alternative orientation allows the uniplanar tulip assembly 551 to angle in, for example, and without limitation, the medial-lateral direction while maintaining rigidity in the cephalad-caudal direction of a body.

The present invention also provides an insertion tool 600 that comprises a spring-loaded, self-retaining tip 602. FIG. 18A-18D respectively illustrate: (i) loading the adapter 502, (ii) inserting the adapter 502 into the recess 24 of the polyaxial bone fastener head 16, (iii) releasing the adapter 502 and coupling the uniplanar tulip assembly 551 onto the bone fastener head 16, and (iv) the misalignment of the adapter 502 during the insertion step.

Figures 18A, 18B, 18C, 18D:
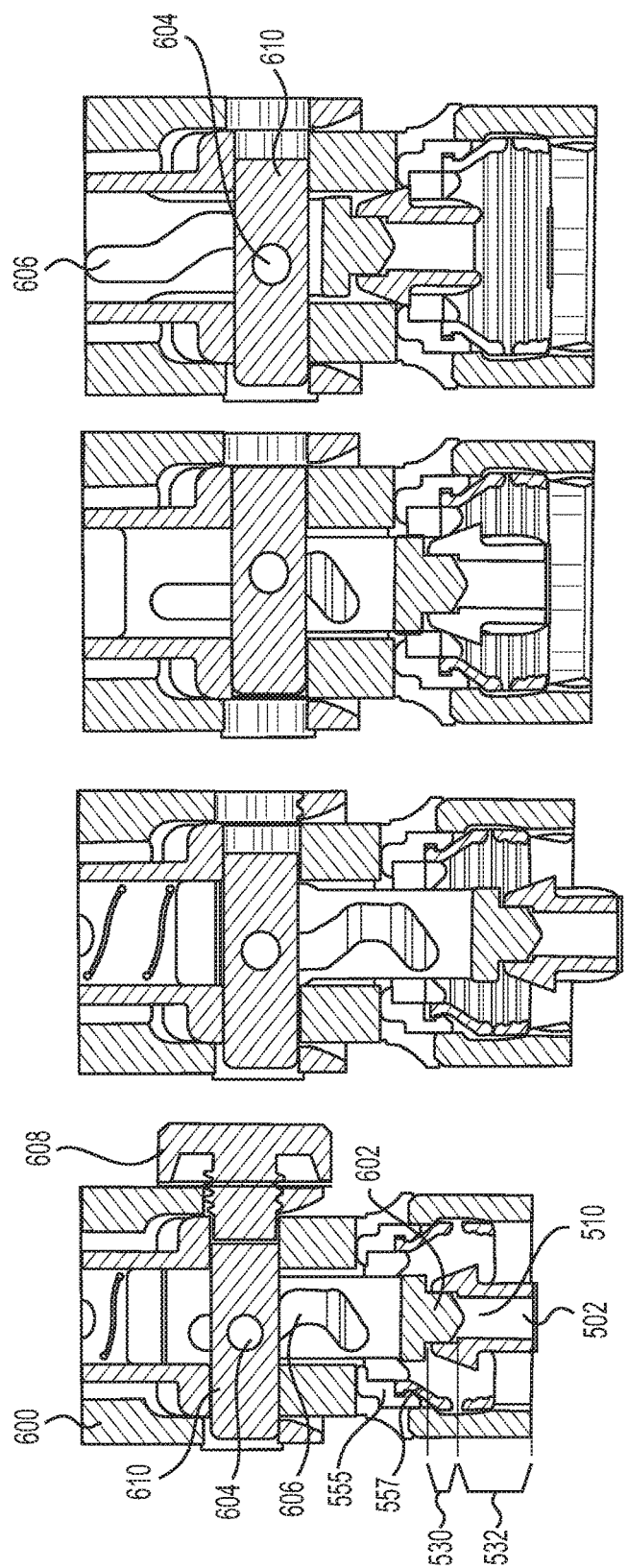
FIGS. 18A-18D is a cross-sectional view of an insertion tool for inserting the adapter in accordance with the present invention.

As shown these figures, the self-retaining tip is sized and shaped to be inserted into a hole 510 of the adapter 502. As a surgeon inserts the self-retaining tip 602 into an upper hole 530 of the hole 510, the self-retaining tip will retract upwards into the housing of the insertion tool 600, as shown in FIG. 18A. To prevent the self-retaining tip 602 from retracting too far up into the housing, a knob 608 is provided. The knob is adapted to restrict an internal pin 604 from traversing a return channel 606. Once the adapter 502 has been loaded into the insertion tool 600, along with the uniplanar tulip assembly 551, the surgeon can remove the knob 608 from the insertion tool 600.

Once the knob 608 is removed from the insertion tool 600, the surgeon aligns the lower portion 504 of the adapter 502 with the recess 24 of the polyaxial bone fastener head 16, as shown in FIG. 18B. The pin 604 will traverse the return channel 606 as the lower portion 504 of the adapter abuts against the bottom of recess 24 (aligned) or the outer surface of the bone fastener head 16 (misaligned). As the pin 604 traverses the return channel 606, it simultaneously moves a blocking mechanism 610 from left to right, as shown in FIG. 18C. During this stage, the surgeon will be listening for a sound or physical feedback from the uniplanar tulip assembly 551. These indications signify that the lower portion 504 of the adapter 502 has been properly aligned and seated within the recess 24. More specifically, the sound or physical feedback is an indication that the tulip assembly 551 is now seated in the bone fastener head 16 and the blocking mechanism 610 has reached a predefined location within insertion tool 600 (as shown in FIG. 18C), at which point the surgeon can engage a handle on the insertion tool 600 so that the tulip assembly 551 can be clamped (via the locking clamp assembly 559) onto the polyaxial bone fastener head 16. However, if the lower portion 504 of the adapter 502 is misaligned with the recess 24, the pin 604 will traverse too far along the return channel 606, thereby causing the blocking mechanism 610 to continue blocking the handle from being able to be operated by the surgeon (as shown in FIG. 18D).

In alternative embodiments, a surgeon can simply insert the lower portion 504 of the adapter 502 into the recess 24 of the polyaxial bone fastener head 16. In this alternative embodiment, the self-retaining tip 602 of the insertion tool 600 will be inserted into the upper hole 530 while the lower portion 504 of the adapter 502 is seated in the recess 24. When the tip 602 is aligned with the upper hole 530 and has been successfully inserted into the upper hole, the blocking mechanism 610 will move to a particular position within the insertion tool 600, as shown in FIG. 18C. It should be noted that the upper portion 506 of the adapter 502 is also inserted into the longitudinal slot 561 when the tip 602 has been successfully inserted into the upper hole 530. At this point, the surgeon can engage a handle on the insertion tool 600 to clamp the tulip assembly 551 onto the bone fastener head 16, as discussed above. If the tip 602 is misaligned with the upper hole 530, the pin 604 will traverse too far along the return channel 606, thereby causing the blocking mechanism 610 to continue blocking the handle from being able to be operated by the surgeon (as shown in FIG. 18D).

A method of using the modular uniplanar pedicle screw assembly 575 on a polyaxial bone fastener 4 that has been inserted into a vertebrae will now be described. The bone faster 4, with the polyaxial tulip assembly 101 coupled thereto, is inserted into a vertebrae. At some point during the surgery, the surgeon may determine intra-operatively that deformity correction is needed at the affected vertebral body and that a uniplanar assembly would be more suitable for this purpose. In accordance with the illustrative embodiment of the present invention, the surgeon can use a specialized tool to decouple the polyaxial tulip assembly 101 from the polyaxial bone fastener 4; in particular, the bone fastener head 16. Once the polyaxial tulip assembly 101 has been decoupled, the surgeon may inserting the lower portion 504 of the adapter 502 into the recess 24 arranged on the head 16 of the polyaxial bone fastener 4. Similarly, the upper portion 506 of the adapter 502 is inserted into the longitudinal slot 561 of the uniplanar tulip assembly 551, as discussed above with respect to FIGS. 18A-18C. The upper portion 506 is adapted to slide along the longitudinal slot 561 to allow movement of the uniplanar tulip assembly 551 in a first plane along a direction that is parallel to a longitudinal axis of the longitudinal slot, while preventing movement of the uniplanar tulip assembly 551 in a second plane lateral to the first plane relative to the bone fastener 4. Once the upper and lower portions of the adapter have inserted, and the uniplanar tulip assembly 551 has been coupled onto the bone fastener head 16, the surgeon attaches a fusion bar to the uniplanar tulip assembly. More specifically, the surgeon may seat the fusion bar 14 on the U-shaped channel 68 of the saddle element 555. A locking cap 12, for example, is threaded onto the uniplanar tulip assembly 575 to lock it onto the bone fastener head 16. Thereafter, the surgeon may move the affected vertebrae to a desired position in the second plane using the uniplanar tulip assembly 575 with the inserted adapter 502 and the attached fusion bar 14.

A Modular Uniplanar Tulip Assembly Having a Pivoting Saddle Element

Figure 19C:
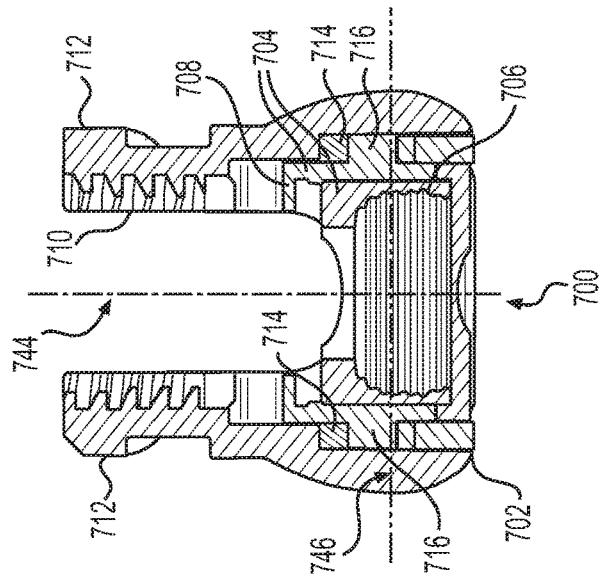
FIG. 19C is a cross-sectional front view of the modular uniplanar tulip assembly of FIG. 19A in accordance with an alternative embodiment of the present invention.
Figure 19B:
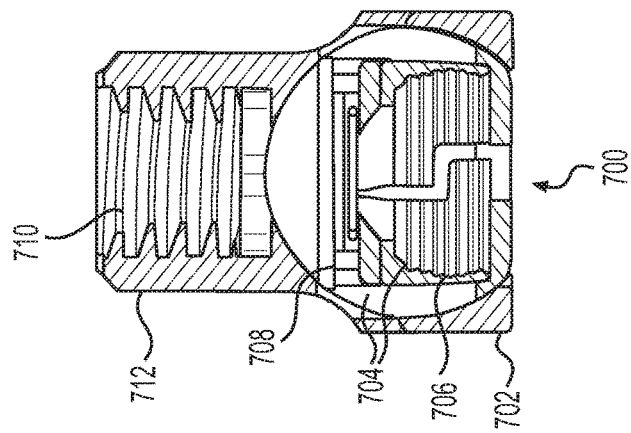
FIG. 19B is a cross-sectional side view of the modular uniplanar tulip assembly of FIG. 19A in accordance with an alternative embodiment of the present invention.
Figure 19A:
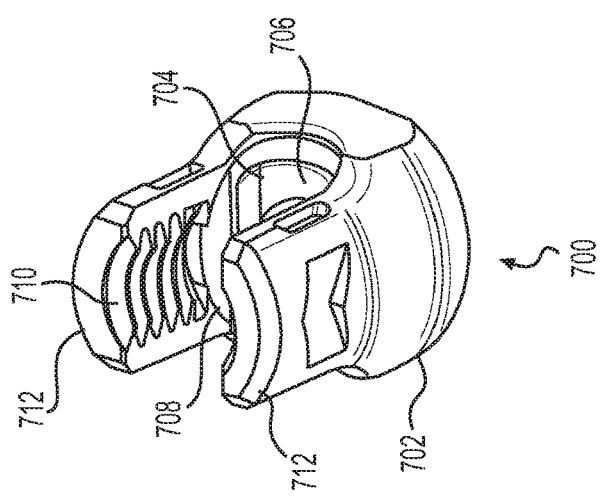
FIG. 19A is a perspective view of a modular uniplanar tulip assembly in accordance with an alternative embodiment of the present invention.

FIG. 19A is a perspective view of a uniplanar tulip assembly 700 in accordance with an alternative embodiment of the present invention. FIGS. 19B and 19C respectively show side and front cross-sectional views of the tulip assembly 700. FIG. 20 depicts the elements that form the tulip assembly 700.

FIGS. 19A-19C show the uniplanar tulip assembly 700 having a tulip element 702 and a locking clamp assembly 704 (which comprises the clamp element 706 and the saddle element 708 depicted in FIG. 20). The locking clamp assembly 704 can be assembled and installed into the tulip element 702 in the same or similar fashion as the locking clamp assembly 6 discussed above, with respect to FIGS. 1-14. Although not shown in FIGS. 19A-19C, the polyaxial pedicle screw assembly 700 also comprises a bone fastener and a locking cap assembly, each of which can be the same as or different than the bone fastener 4 and locking cap assembly 12 discussed above.

In general, the tulip assembly 700 is similar to the tulip assembly 101 depicted in FIG. 1, with the exception that the saddle element 708 may not have a longitudinal slot 561 for receiving an adapter 502. Instead, to be able to use the uniplanar tulip assembly 700 with the polyaxial bone fastener 4, the inner surface 710 of each oppositely positioned lateral arm 712 of the tulip element 702 is arranged with a recess 714 (e.g., keyhole, etc.) that is adapted to receive a corresponding protrusion 716 of the saddle element 708.

More specifically, FIG. 19B depicts the clamp element 706 and the saddle element 708 assembled to form the locking clamp assembly 704. The clamp element 706 includes at least one slit 738 that divides the clamp element into a first clamp portion 726 and a second clamp portion 728. The at least one slit 738 may, for example, allow the first and second clamp portions 726, 728 to constrict and securely engage the head 16 of the bone fastener 4. FIG. 19B, however, depicts the tulip element 702 in an unlocked position (e.g., as discussed above with respect to FIG. 6). In the unlocked position, the tulip element 702, clamp element 706, and saddle element 708 are allowed to, as a single unit, rotate about a central axis (i.e., the rotation axis 746 of FIG. 19C) of the bone fastener 4 and pivot/angulate freely about the bone fastener head 16.

At some point in time, the surgeon may cause the first and second clamp portions 726, 728 to constrict and engage the head 16 of the bone fastener 4, thereby placing the clamp element 706 and the saddle element 708 in a locked position (e.g., as discussed above with respect to FIG. 7). In the locked position, the tulip element 702, clamp element 706, and saddle element 708 can no longer rotate about the central axis of the bone fastener 4. The locked position further disallows the clamp element 706 and the saddle element 708 from pivoting/angulating in any and all planes of the bone fastener head 16. The only element that is allowed to pivot/angulate in the locked position is the tulip element 702, which element is only allowed to pivot/angulate in a single plane of the polyaxial bone fastener head 16. That is, since each of the oppositely positioned lateral protrusions 716 of the saddle element 708 is sized and shaped to be received in a respective recess 714 arranged on the inner surface 710 of the tulip element 702, the tulip element 702 is allowed to pivot/angulate along the articulating plane 744 depicted in FIG. 19C. The articulating plane can be, for example, and without limitation, the medial-lateral direction or the cephalad-caudal direction of a body. When the surgeon wishes to re-adjust the pivoting/angulation plane of the tulip element 702, the surgeon may place the tulip assembly in the unlocked position using a tool and repeat the steps above.

By employing this configuration, a surgeon can have the flexibility of polyaxial angulation of a pedicle screw and the ability to independently lock the screw into uniplanar or bi-planar angulation to provide rigidity in a particular plane.

Figure 21:
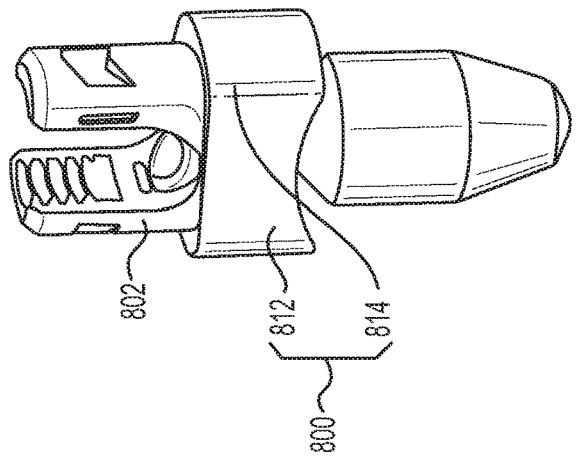
FIG. 21 is a perspective view of pedicle screw coupled to a sleeve assembly for converting the pedicle screw to a uniplanar pedicle screw in accordance with an alternative embodiment of the present invention.

A Tulip Sleeve for Converting a Polyaxial Pedicle Screw to a Uniplanar Pedicle Screw FIG. 21 is a perspective view of a polyaxial pedicle screw that can be converted to a uniplanar pedicle screw using a sleeve assembly 800 in accordance with an alternative embodiment of the present invention.

Figure 22:
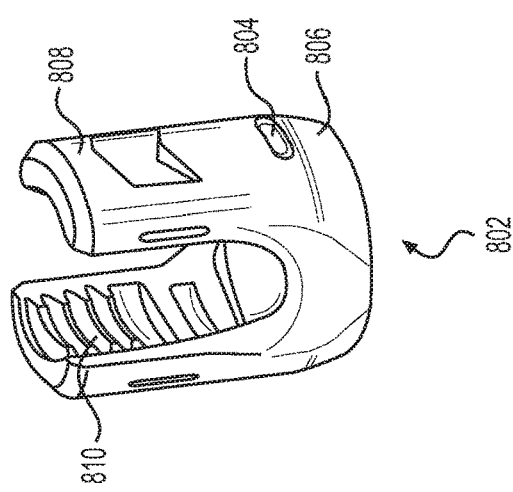
FIG. 22 is a perspective view of a tulip element having one or more slots for receiving an insert of a sleeve assembly in accordance with an alternative embodiment of the present invention.

In this alternative embodiment of the present invention, the tulip elements 10, 702 can be modified to receive a sleeve assembly 800 for preventing the tulip assembly from pivoting or angulating in a particular plane of the bone fastener head 16. As shown in FIG. 22, tulip element 802 (which can have substantially the same or different structural, physical, and/or functional characteristics as tulip elements 10, 702 discussed above) comprises a recess 804 that is arranged at a lower portion of the outer surface 806 of a lateral arm 808. It will be clear to those skilled in the art, after reading this disclosure, that the other lateral arm 810 is substantially identical to and a mirror image of the lateral arm 808. The recess 804 of each lateral arm 808, 810 is sized and shaped to receive and complement a corresponding insert 816 for attaching the sleeve assembly 800 to the tulip element 802. The inserts 816 fit squarely into the recesses 804 to provide the functionality of preventing the sleeve assembly 800 from axial and rotational movement relative to the tulip element 802.

Figure 23:
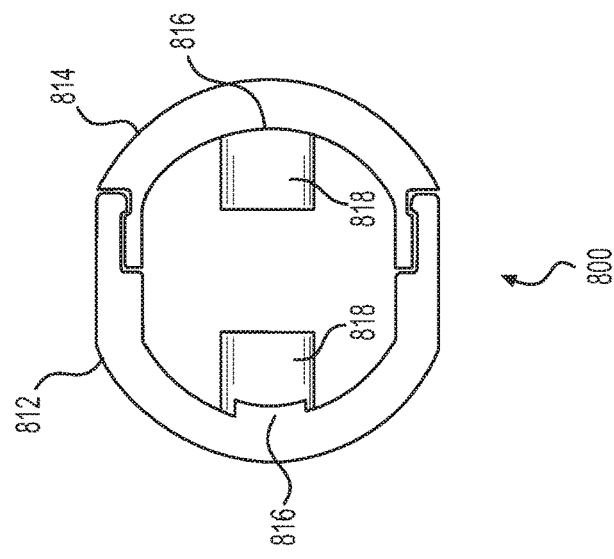
FIG. 23 is a top view of the sleeve assembly of FIG. 21 in accordance with an alternative embodiment of the present invention.

As shown in FIG. 23, the sleeve assembly 800 is constructed and arranged with a first portion 812 and a second portion 814. The portions are joined together to form the sleeve assembly 800 depicted in the figure. Each of the first and second portions 812, 814 include a pin 818. When the sleeve assembly 800 is attached to the tulip element 802 via the inserts 816, the bottom surface of the bone fastener head 16 rests on top of the pins 818, while the shaft 18 of the bone fastener 4 comes into secure engagement with the inwardly protruding pins 818. This secure engagement between the pins 818 and the shaft 18 prevents the tulip element 802 from pivoting in the medial-lateral section of a body, while allowing pivoting of the tulip element 802 in the cephalad-caudal section of the body.

Uniplanar Pedicle Screw Assembly Having Rotational and Translational Capabilities FIG. 24A is a perspective view of a uniplanar pedicle screw assembly 900 that allows a bone fastener 4 to have: (i) rotational movement (e.g., pivoting or angulate) in a first plane along a direction that is perpendicular to a longitudinal axis of a translation rod and (ii) translational movement in a second plane along a direction that is parallel to the longitudinal axis of the translation rod.

FIG. 24B depicts the uniplanar pedicle screw assembly 900 of FIG. 24A disassembled. As shown in the figure, the assembly 900 comprises a tulip element 904 having a body 906 and a pair of oppositely positioned lateral arms 908. Tulip element 904 can be substantially the same as or different than the tulip elements discussed above. In this embodiment of the present invention, each arm 908 includes a slot 910 (only one is shown in the figure) that is sized and shaped to receive and complement a corresponding saddle retainer 912. Further, each lateral surface of the body 906 includes a through-hole 914 (only one is shown in the figure) that is sized and shaped to receive and complement a translation rod 916 for allowing the bone fastener 4 to have rotational and translational capabilities. It will be clear to those skilled in the art, after reading this disclosure, that one half of the tulip element 904 is substantially identical to and a mirror image of the other half of the tulip element. It will also be clear to those skilled in the art that tulip element 904 can have substantially the same or different structural, physical, and/or functional characteristics as tulip elements 10, 702 discussed above. FIG. 24B further depicts a saddle element 902 and a bone fastener 4 having a head 16 arranged with a pair of oppositely positioned through-holes 918 (only one is shown in the figure) that is sized and shaped to receive and complement a translation rod 916. In this embodiment of the invention, the pair of oppositely positioned through-holes 918 of the bone faster head has a similar functionality as a yoke. It will be clear to those skilled in the art, after reading this disclosure, that one half of the bone fastener head 16 is substantially identical to and a mirror image of the other half of the bone fastener head.

Figure 25B:
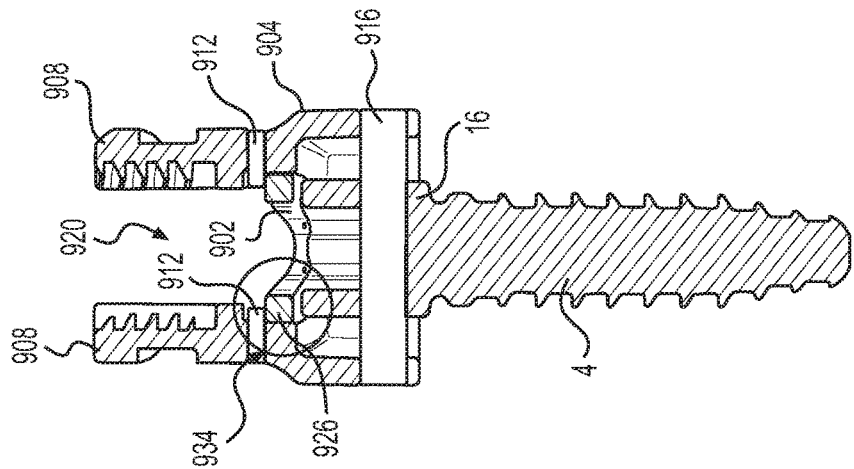
FIG. 25B is a cross-sectional front view of the pedicle screw assembly of FIG. 25A in accordance with an alternative embodiment of the present invention.
Figure 25A:
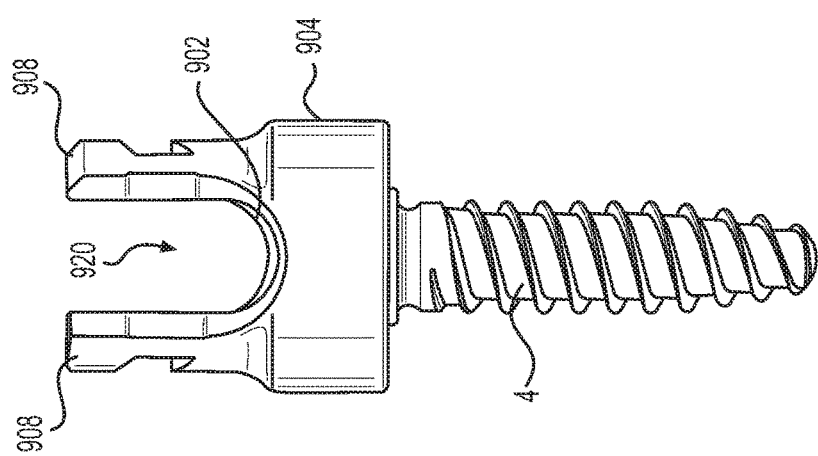
FIG. 25A is a front view of the pedicle screw assembly of FIG. 24A in accordance with an alternative embodiment of the present invention.

FIG. 25A is a front view of the uniplanar pedicle screw assembly 900 of the present invention. FIG. 25B is a cross-sectional view of the uniplanar pedicle screw assembly 900 of FIG. 25A. As shown in the figure, each of the slots 910 is sized and shaped to receive a saddle retainer 912. The upper and lower surfaces of the saddle retainer 912 come into secure engagement with the corresponding surfaces of the slot 910 when inserted therein. Each of the saddle retainers 912 extend beyond the upper and lower surfaces of their respective slot 910 in order to engage an upper lip 926 of the saddle element 902. This configuration retains the saddle element 902 within the bore 920 of the tulip element 904. Also shown in FIG. 25B is the bone fastener 4 coupled to the tulip element 904 via the translation rod 916. Each of the through-holes 918 arranged on the bone fastener head 16 is aligned with their respective through-hole 914 arranged on the tulip element 904. Once aligned, the translation rod 916 is inserted through the through-holes 914, 918. The ends of the translation rod 916 are peened to ensure that the rod does not fall out of the through-holes. It should be noted at this point of the disclosure that there is a small gap 934 between the bone fastener head 16 and the saddle element 902. As will be described in more detail below, this small gap 934 provides clearance to allow the tulip element 904 to pivot or angulate in a particular plane.

FIG. 26A is a side view of the uniplanar pedicle screw assembly 900 of the present invention. FIG. 26B is a cross-sectional view of the uniplanar pedicle screw assembly 900 of FIG. 26A. As shown in the figure, the saddle element 902 is arranged with a pair of oppositely positioned teeth 922, each of which is adapted to engage an upper surface of the bone fastener head 16 to restrict rotational movement of the tulip element 904 (relative to a central axis of the bone fastener 4) to a predefined range. As further shown in the figure, the translation rod 916 enables the tulip element 916 to have rotational movement (e.g., pivoting or angulate) in a first plane along a direction that is perpendicular to a longitudinal axis of the translation rod 916. The rotational movement is made possible by the small gap 934, which provides clearance between the saddle element 902 and the bone fastener head 16.

Figure 27A:
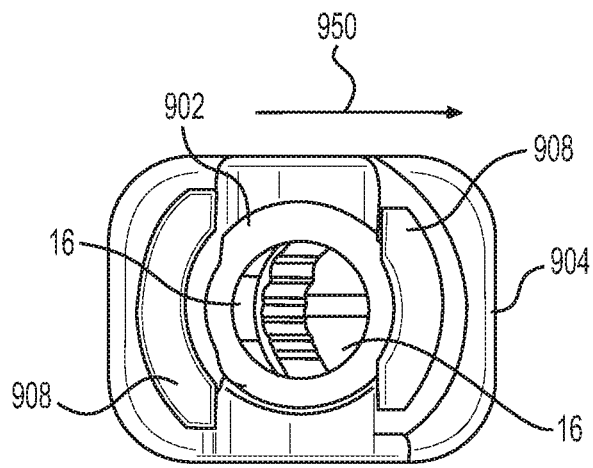
FIG. 27A is a top view of the pedicle screw assembly of FIG. 24A showing translational movement of the tulip element relative to the bone faster in accordance with an alternative embodiment of the present invention.
Figure 27B:
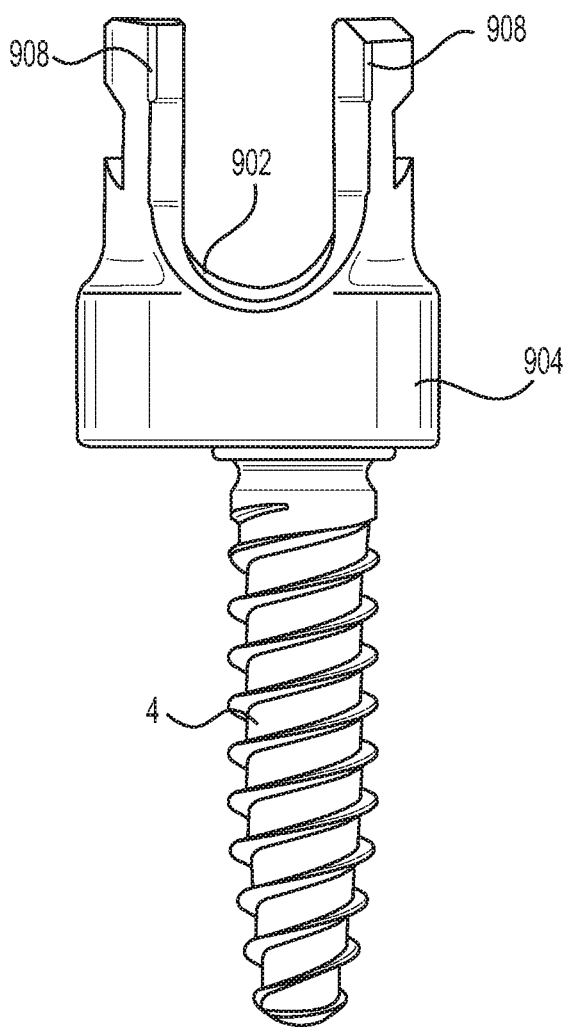
FIG. 27B is a front view of the pedicle screw assembly of FIG. 27A showing translational movement of the tulip element relative to the bone faster in accordance with an alternative embodiment of the present invention.

FIG. 27A is top view of the uniplanar pedicle screw assembly 900 of the present invention, with the top view showing translational movement of the tulip element 904 towards the arrow 950. FIG. 27B is a front view of the translated uniplanar pedicle screw assembly 900 of FIG. 27B. As shown in the figures, not only does the translation rod 916 enable the tulip element 904 to pivot or angulate, it also enables the tulip element 904 to have translational movement in a second plane along a direction that is parallel to the longitudinal axis of the translation rod 916.

Figure 28:
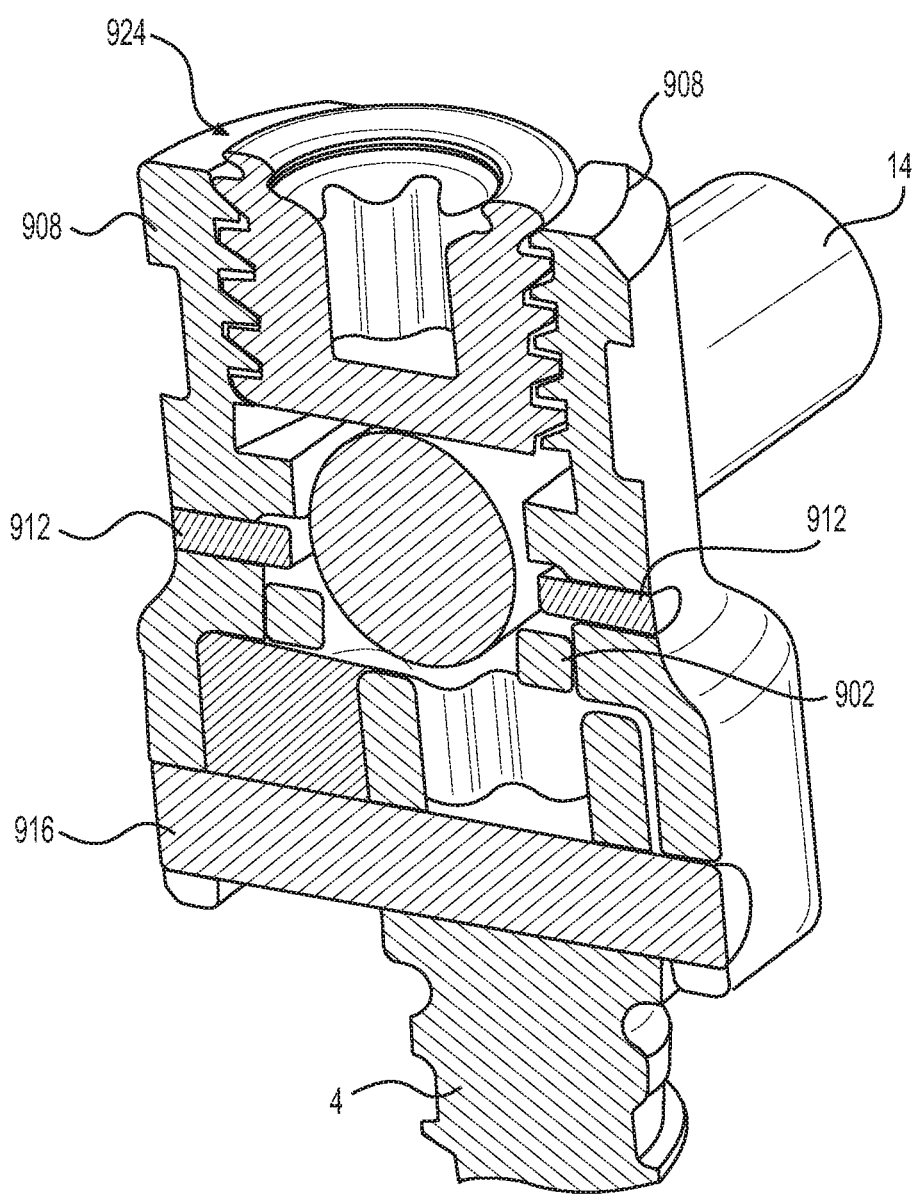
FIG. 28 is a cross-sectional view of the pedicle screw assembly of FIG. 24A with a fusion rod and a locking cap assembly in accordance with an alternative embodiment of the present invention.

Once the tulip element 904 has been rotated or translated to a desired position, a locking mechanism is used to secure the tulip element 904 in that position. As shown in FIG. 28, a fusion rod 14 is seated on an upper surface of the saddle element 902 and a locking cap 924 is threaded onto the pair of oppositely positioned lateral arms 908 of the tulip element 904. The bottom surface of the locking cap 924 abuts against the fusion rod 14, which in turn causes the saddle element 902 to constrain movement of tulip element 904 relative to the bone fastener head 16.

It is to be understood that the disclosure describes a few embodiments and that many variations of the invention can easily be devised by those skilled in the art after reading this disclosure and that the scope of the present invention is to be determined by the following claims.

We claim:

1. A modular uniplanar pedicle screw assembly comprising:
   a uniplanar tulip assembly comprising a detachable tulip configured to couple to a head of a bone fastener, the uniplanar tulip assembly further comprising a saddle having an upper surface and a lower surface and including a longitudinal slot extending through the saddle from the upper surface to the lower surface, and a clamp; and
   an adapter including:
   (i) a lower portion sized and shaped to be received in a recess of the head of the bone fastener, and
   (ii) an upper portion extending from the lower portion, the upper portion having an upper surface, a pair of oppositely positioned lateral surfaces extending from the upper surface, and a pair of oppositely positioned inclined surfaces extending from the upper surface, the inclined surfaces configured to be received into the longitudinal slot of the saddle to allow movement of the uniplanar tulip assembly in a first plane along a direction that is parallel to a longitudinal axis of the longitudinal slot, the longitudinal slot preventing movement of the uniplanar tulip assembly in a second plane lateral to the first plane relative to the bone fastener, wherein the clamp has a non-linear slot.

2. The modular uniplanar pedicle screw assembly of claim 1, wherein the upper portion has a pair of oppositely positioned lateral surfaces that abut against respective oppositely positioned inner walls of the longitudinal slot to prevent movement of the uniplanar tulip assembly in the second plane.

3. The modular uniplanar pedicle screw assembly of claim 1, wherein the upper portion has a pair of oppositely positioned inclined surfaces that abut against respective oppositely positioned inner walls of the uniplanar tulip assembly to stop the upper portion from sliding past a predefined location along the longitudinal slot.

4. The modular uniplanar pedicle screw assembly of claim 1, wherein the lower portion is shaped to complement the shape of the recess to prevent the adaptor from rotating about a central axis of the bone fastener head.

5. The modular uniplanar pedicle screw assembly of claim 4, wherein the lower portion is torx-shaped.

6. The modular uniplanar pedicle screw assembly of claim 1, wherein lower portion has a cylindrical shape to allow the adapter to rotate about a central axis of the bone fastener head.

7. The modular uniplanar pedicle screw assembly claim 1, wherein the adapter has a hole for receiving a self-retaining tip of an insertion tool.

8. The modular uniplanar pedicle screw assembly of claim 7, wherein the hole includes a through-hole having an upper hole for receiving the self-retaining tip and a lower hole whose diameter is smaller than the upper hole.

9. The modular uniplanar pedicle screw assembly of claim 1, wherein the bone fastener head is also adapted to be coupled to a polyaxial tulip assembly, wherein the polyaxial tulip assembly is adapted to polyaxially move about a central axis of the bone fastener head.

10. The modular uniplanar pedicle screw assembly of claim 1, wherein the inclined surfaces form a flange having an underside that rests on top of the head of the bone fastener.

11. The modular uniplanar pedicle screw assembly of claim 1, wherein the saddle includes a pair of oppositely positioned lateral protrusions each sized and shaped to be received in a corresponding recess arranged on an inner surface of the tulip.

12. The modular uniplanar pedicle screw assembly of claim 1, wherein the tulip includes a body and a pair of oppositely positioned lateral arms extending upwardly from the body, and the arms define a U-shaped channel sized to receive a rod.

13. A modular uniplanar pedicle screw assembly comprising:

a bone fastener having a head defining a recess and a shaft extending from the head;

a uniplanar tulip assembly comprising a detachable tulip having a bottom opening for receiving the head of the bone fastener, a saddle having an upper surface and a lower surface and defining a longitudinal slot extending through the saddle from the upper surface to the lower surface, and a clamp defining a non-linear slot; and an adapter including:

(i) a lower portion sized and shaped to be received in the recess of the head of the bone fastener, and (ii) an upper portion extending from the lower portion, the upper portion having an upper surface, a pair of oppositely positioned lateral surfaces extending from the upper surface, and a pair of oppositely positioned inclined surfaces extending from the upper surface, the inclined surfaces configured to be received into the longitudinal slot of the saddle to allow movement of the uniplanar tulip assembly in a first plane along a direction that is parallel to a longitudinal axis of the longitudinal slot, the longitudinal slot preventing movement of the uniplanar tulip assembly in a second plane lateral to the first plane relative to the bone fastener.

* * * * *